US005965119A

United States Patent [19]
Greenwald et al.

[11] Patent Number: 5,965,119
[45] Date of Patent: Oct. 12, 1999

[54] TRIALKYL-LOCK-FACILITATED POLYMERIC PRODRUGS OF AMINO-CONTAINING BIOACTIVE AGENTS

[75] Inventors: Richard B. Greenwald, Somerset; Yun H. Choe, Piscataway, both of N.J.

[73] Assignee: Enzon, Inc., Piscataway, N.J.

[21] Appl. No.: 09/000,676

[22] Filed: Dec. 30, 1997

[51] Int. Cl.⁶ .................................................. A61K 31/765
[52] U.S. Cl. .................... 424/78.37; 424/85.1; 424/85.2; 424/85.4; 530/351; 530/402; 548/572; 558/230; 558/273; 560/160; 560/170; 560/186
[58] Field of Search ................................ 424/85.1, 85.2, 424/85.4, 78.37; 530/351, 402; 548/572; 558/230, 273; 560/160, 170, 186

[56] References Cited

U.S. PATENT DOCUMENTS

| | | |
|---|---|---|
| 4,179,337 | 12/1979 | Davis et al. . |
| 5,093,531 | 3/1992 | Sano et al. . |
| 5,112,739 | 5/1992 | Meneghini et al. . |
| 5,122,614 | 6/1992 | Zalipsky . |
| 5,321,095 | 6/1994 | Greenwald . |
| 5,349,001 | 9/1994 | Greenwald et al. . |
| 5,561,119 | 10/1996 | Jacquesy et al. . |
| 5,605,976 | 2/1997 | Martinez et al. . |
| 5,643,575 | 7/1997 | Martinez et al. . |
| 5,672,584 | 9/1997 | Borchardt et al. . |
| 5,710,135 | 1/1998 | Leenders et al. . |

OTHER PUBLICATIONS

STN Registry File #164792–14–7, 1995.
Totani et al. "Preparation of Chroman Derivatives". STN CAPCUS, Abstract #1995:667328, 1995.
Shearwater Polymers, Inc., Catalog–*Polyethylene Glycol Derivatives*, (1998) pp. 8,33.
Leenders, R.G.G.et al., Highly Diatereoselective Synthesis of Anomeric B–O–Glycopyranosyl Carbamates from Isocyanates, Synthesis (Nov. 1996); pp. 1309–1312.
Leenders, R.G.G. et al, B–Glucuronyl Carbamate Based Pro-moieties Designed for Prodrugs in ADEPT, (1995); Tetrahedron Letters vol. 36, No. 10 pp. 1701–1704.
Waldmann, H. et al, Synthesis of the Palmitoylated and Farnesylated C–Terminal Lipohexapeptide of the Human N–Ras Protein by Employing . . . , Angew. Chem Int. Ed. (1995), 34 No. 20; pp. 2259–2262.
Jungheim, L.N. et al., Design of Antitumor Prodrugs: Substrates for Antibody Targeted Enzymes, Chem. Rev.(1994;) 94 pp. 1553–1566.
Bundgaard, H. The Double Prodrug Concept and its Applications, Advanced Drug Delivery Reviews, 3 (1989) pp. 39–65.
Wakselman, M. et al., An Alkali–labile Substituted Benzyloxycarbonyl Amino–protecting Group, JCS Chem. Comm (1973); pp. 593–594.
Carl, P.L. et al. A Novel Connector Linkage Applicable in Prodrug Design, J. Med.Chem (1981) vol. 24, No. 5 479–480.

(List continued on next page.)

*Primary Examiner*—Johann Richter
*Assistant Examiner*—Patrick R. Delaney
*Attorney, Agent, or Firm*—Robert & Mercanti, LLP

[57] ABSTRACT

The present invention is directed to double prodrugs containing polymeric-based transport forms. These polymeric prodrugs are preferably of the formula:

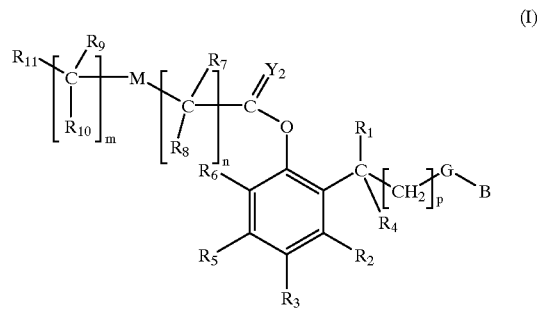

wherein:
B is a leaving group or a residue of an amine-containing target moiety;
G is

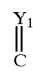

or $CH_2$;
$Y_{1-2}$ are independently O or S;
M is X or Q; where X is an electron withdrawing group and Q is a moiety containing a free electron pair positioned three to six atoms from $C(=Y_2)$;
$R_1, R_4, R_7, R_8, R_9, R_{10}$ and $R_{13}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls;
$R_2, R_3, R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aralkyls, aryls, substituted aryls, such as aryls substituted with halo-, nitro- and cyano-; carboxy-, $C_{1-6}$ carboxyalkyls and $C_{1-6}$ alkyl carbonyls;
(m) is zero or one;
(n) is zero or a positive integer;
(p) is zero, one or two; and
$R_{11}$ is a substantially non-antigenic polymer.

The first prodrug is generated when the polymeric portion of the double prodrug is cleaved and the parent molecule is generated rapidly thereafter in vivo, as a result of a trialkyl lock type lactonization-type reaction.

42 Claims, 11 Drawing Sheets

OTHER PUBLICATIONS

Wang, B. et al. Synthesis of a Novel Esterase–Sensitive Cuclic Prodrug System for Peptides That Utilizes Utilizes a "Trimethyl Lock" Facilitated Lactonization Reaction J.Org.Chem (1997), 62, 1363–67.

Amsberry, K.L. et al. The Lactonization of 2'–Hydroxyhydrocinnamic Acid Amides: A Potential Pro fro Amines, J.Org.Chem (1990) 55 5867–5877.

Wang, B. et al. Chemical Feasibility Studies of a Potential Coumarin–BAsed Prodrug System, Bioorganic & Medicinal Chemistry Letters, vol. 6, No. 8, pp. 945–950, (1996).

Wang et al Coumarin–based Prodrugs 2. Synthesis and Bioreversibility Studies of an Esterase–Sensitive Cycli Prodrug of DADLE... Bioorg. & Med. Chem.L ett vol. 6, No. 23 2823–26, (1996).

Amsberry, K et al. Amine Prodrugs Which Hydrolyze Amide Lactonization. I. A potential Redox–Sensitive Amide Prodrug, Pharmaceutical Research vol. 8, No. 3,(1991).

Carpino, L.A., Reductive Lactoinization of Strategically Methylated Quinone Propionic Acid Ester Amids, J.Org.Chem (1989) 54 53303–3310.

Shan, D., et al., Prodrug Strategies Based on Intramolecular Cyclization Reactions, Journal of Pharmaceutical Sciences, (Jul. 1997.) vol. 86, NO. 7, pp. 765–767.

TRIALKYL-LOCK-FACILITATED POLYMERIC PRODRUGS OF AMINO-CONTAINING BIOACTIVE AGENTS

TECHNICAL FIELD

The present invention relates to double prodrugs. In particular, the invention relates to polymeric-based double prodrugs having reversible linkages involving amino moieties of chemical compounds and biologically active materials such as enzymes, proteins and the like.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal agent is either insoluble in aqueous fluids or is rapidly degraded in vivo. For example, alkaloids are often especially difficult to solubilize.

One way to solubilize medicinal agents is to include them as part of a soluble prodrug. Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols. See *Remington's Pharmaceutical Sciences,* 16th Ed., A. Osol, Ed. (1980), the disclosure of which is incorporated by reference herein.

Prodrugs are often biologically inert, or substantially inactive, forms of the parent or active compound. The rate of release of the active drug, i.e. the rate of hydrolysis, is influenced by several factors but especially by the type of bond joining the parent drug to the modifier. Care must be taken to avoid preparing prodrugs which are eliminated through the kidney or reticular endothelial system, etc. before a sufficient amount of hydrolysis of the parent compound occurs. By incorporating a polymer as part of the prodrug system, one can increase the circulating half-life of the drug. However, in some situations such as with alkaloids, it has been determined that when only one or two polymers of less than about 10,000 daltons are conjugated thereto, the resulting conjugates are rapidly eliminated in vivo especially if a somewhat hydrolysis-resistant linkage is used. In fact, such conjugates are so rapidly cleared from the body that even if a hydrolysis-prone ester linkage is used, not enough of the parent molecule is regenerated in vivo. This is often not a concern with moieties such as proteins, enzymes and the like even when hydrolysis-resistant linkages are used. In those cases multiple polymer strands, each having a molecular weight of about 2–5 kDa, are used to further increase the molecular weight and circulating half-life.

Although the above-mentioned concept of prodrug-based delivery systems has proven to be useful in many instances, there are nonetheless situations where alternatives are desired. For example, Bundgaard in "The Double Prodrug Concept and Its Applications" in *Advanced Drug Delivery Reviews,* 3 (1989) 39–65, (the contents of which are hereby incorporated by reference) pointed out that in many cases it is difficult to obtain a prodrug which has the proper combination of adequate stability in vitro and high susceptibility to regenerate the parent drug in vivo. As pointed out by Bundgaard, a promising means of overcoming some of the previously encountered shortcomings involves the use of cascade latentiation or "pro-prodrugs". In such systems, the hydrolytic reaction sequence involves a first step which usually is an enzymatic cleavage and the second involves a non-enzymatic hydrolysis that occurs only after the first has taken place.

It is believed that in spite of the reported work in the field of double prodrugs, some specific problems were not addressed sufficiently. For example, the previously reported techniques do not sufficiently address the solubility problems of many parent compounds. In addition, the problem of designing in a sufficient increase in circulating half-life for the prodrug was also not sufficiently developed. Thus, there continues to be a need to provide additional technologies for forming prodrugs which would benefit from the double prodrug concept. For example, it would be advantageous to provide the artisan with alternative techniques for transport carrier attachment so as to regulate biological effect. Furthermore, it would be desirable to provide additional techniques to address problems associated with involving amino residues of parent compounds and thus avoid excessively fast or slow hydrolysis of the transport form from the parent compound at physiological pH.

SUMMARY OF THE INVENTION

The present invention addresses the shortcomings described above. In one aspect of the invention, compounds of Formula (I) are provided:

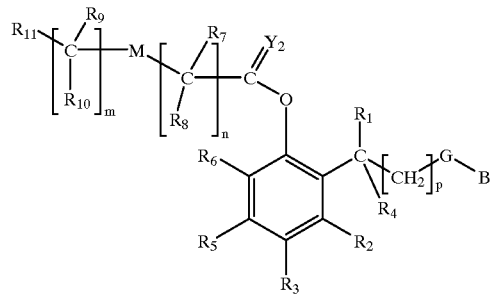

wherein:

B is H, OH, OSiR$_{13}$ or a residue of an amine-containing target moiety;

G is

or CH$_2$;

Y$_{1-2}$ are independently O or S;

M is X or Q; where
   X is an electron withdrawing group
   Q is a moiety containing a free electron pair positioned three to six atoms from C(=Y$_2$);

R$_1$, R$_4$, R$_7$, R$_8$, R$_9$, R$_{10}$ and R$_{13}$ are independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls;

R$_2$, R$_3$, R$_5$ and R$_6$ are independently selected from the group consisting of hydrogen, C$_{1-6}$ alkyls, C$_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aralkyls, aryls, substituted aryls, such as aryls substituted with halo-, nitro- and cyano-; carboxy-, carboxyalkyl, alkylcarbonyl, etc.;

(m) is zero or one;

(n) is zero or a positive integer;

(p) is zero, one or two; and $R_{11}$ is a polymer such as a water-soluble polyalkylene oxide, preferably of relatively high molecular weight i.e., ≧about 20,000 Daltons, for drugs and from about 2,000 to about 20,000 Daltons for proteins, enzymes and the like.

In some preferred embodiments, $R_2$ and $R_5$ are $C_{1-6}$ alkyl moieties such as methyl and $R_3$ and $R_6$ are both preferably hydrogen.

In certain preferred aspects, B is a leaving group such as N-hydroxybenzotriazolyl, N-hydroxyphthalimidyl, halogen, p-nitrophenoxy, imidazolyl, N-hydroxysuccinimidyl, thiazolidyl thione, or other activating groups. Alternatively, B is a residue of any amino-containing compound for which one or more of improved aqueous solubility, decreased antigenicity, prodrug and/or controlled release delivery is desired. For example, B, can be a residue of an enzyme, protein, or organic compound such as daunorubicin, doxorubicin, p-aminoaniline mustard, etc.

For purposes of the present invention, the term "residue" shall be understood to mean that portion of a biologically active compound which remains after it has undergone a substitution reaction in which the prodrug carrier portion has been attached. For purposes of the present invention, the term "alkyl" shall be understood to include straight, branched, substituted $C_{1-12}$ alkyls, including alkoxy, $C_{3-8}$ cycloalkyls or substituted cycloalkyls, etc.

The double prodrugs of the present invention are thus unique delivery systems. Preferably the polymeric portion is first released by hydrolysis and then the resultant "second prodrug" moiety undergoes a cyclization reaction to regenerate the amine-containing bioactive compound.

Some of the chief advantages of the double prodrug compounds of the present invention are that they are capable of solubilizing amine-containing compounds and extending their half-life as compared to the native or even "second" prodrug counterparts. The linkage between the polymer and the "second prodrug" compound as described above, hydrolyzes at a rate which allows the compound to retain its enhanced solubility and circulating half-life. The native drug, however, is still not released at this point. Only after the "second prodrug" undergoes a trialkyl lock lactonization reaction, will the desired native molecule be released. It is readily apparent that this double prodrug approach of the present invention offers unique and unexpected characteristics which enhance the circulating half-life and solubility of native molecules.

Methods of making and using the compounds and conjugates described herein are also provided.

DETAILED DESCRIPTION OF THE INVENTION

A. Formula (I)

Figure 1:
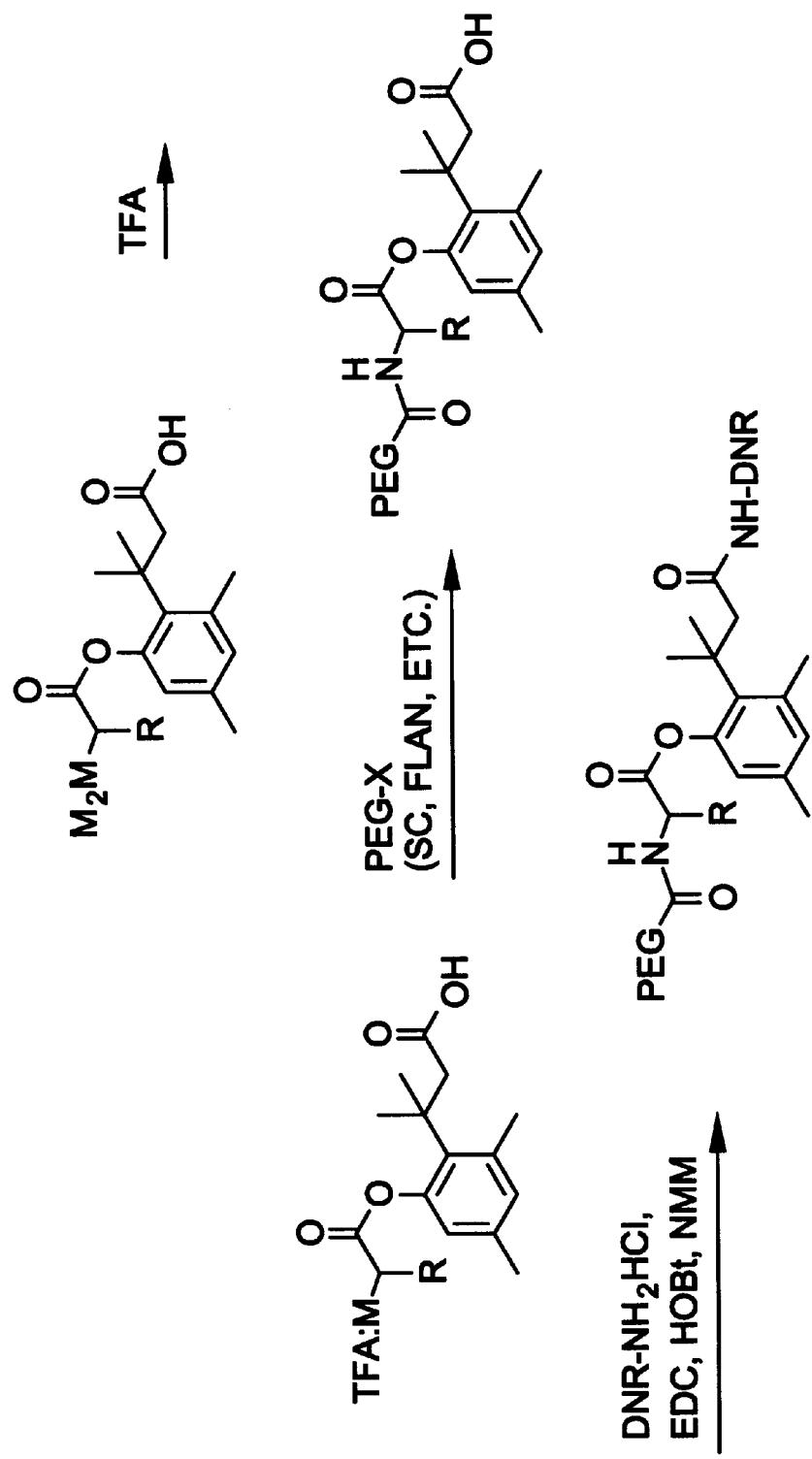
FIGS. 1–2 schematically illustrate two methods of forming double prodrugs of the present invention.

In one aspect of the invention, there are provided compounds of formula (I):

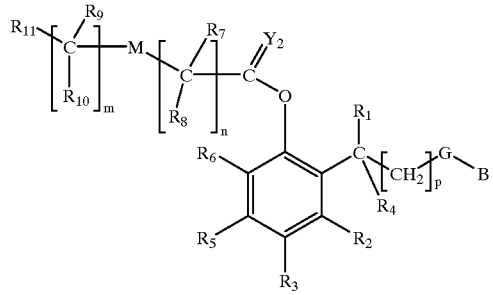

wherein:

B is H, OH, $OSiR_{13}$ or a residue of an amine-containing target moiety;

G is

or $CH_2$;

$Y_{1-2}$ are independently O or S;

M is X or Q; where
 X is an electron withdrawing group
 Q is a moiety containing a free electron pair positioned three to six atoms from $C(=Y_2)$;

$R_1$, $R_4$, $R_7$, $R_8$, $R_9$, $R_{10}$ and $R_{13}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aralkyls, aryls, substituted aryls, such as aryls substituted with halo-, nitro- and cyano-; carboxy-, carboxyalkyl, alkylcarbonyl, etc.;

(m) is zero or one;

(n) is zero or a positive integer;

(p) is zero, one or two; and $R_{11}$ is a substantially non-antigenic polymer.

B. Preferred Aspects of Benzyl Portion of Formula (I)

In preferred aspects of the present invention, $R_2$ and $R_5$ are independently $C_{1-6}$ alkyls. More preferably, $R_2$ and $R_5$ are both methyl. Furthermore, $R_3$ and $R_6$ are preferably both hydrogen, $R_1$, $R_4$, $R_9$ and $R_{10}$ are preferably either hydrogen, $CH_3$ or $CH_2CH_3$. $Y_{1-2}$ are preferably O, and (p) is preferably one.

For purposes of the present invention, substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromophenyl; aralkyls include moieties such as toluyl; heteroalkyls include moieties such as ethylthiophene; substituted heteroalkyls include moieties such as 3-methoxythiophene; alkoxy includes moieties such as methoxy; and phenoxy includes moieties such as 3-nitrophenoxy. Halo- shall be understood to include fluoro, chloro, iodo and bromo.

C. The Double Prodrug Linkage Portion

The double prodrug linkages are selected to hydrolyze in vivo at a rate which generates sufficient amounts of the "second" prodrug compound within a suitable time after administration. The term "sufficient amounts" for purposes of the present invention shall mean an amount which may later undergo sufficient trialkyl lock lactonization in vivo to release the native compound and achieve a desired effect. Preferably, (n) is an integer from 1 to about 12. More preferably, (n) is 1 or 2.

1. The Electron Withdrawing Group X

Within the formula (I) described above, M may be X which is designated as an electron withdrawing group. In particular, X can be selected from moieties such as O, $N(R_{12})$, S, SO and $SO_2$ where $R_{12}$ is the same as that defined for $R_1$, i.e. H, $C_{1-6}$ alkyls, branched alkyls, aryls, substituted aryls, $C_{1-6}$ alkyl aralkyls, heteroalkyls, substituted heteroalkyls or substituted $C_{1-6}$ alkyls such as carboxyalkyls, aminoalkyls, dialkylaminos, hydroxyalkyls or mercaptoalkyls, to name but a few. Preferably, however, when X is $N(R_{12})$, $R_{12}$ is H. It is preferred that X is either O or $N(R_{12})$.

2. Q Portion of the Linker

When M is Q, the polymer, $R_{11}$, is preferably attached to Q via a heteroatom such as oxygen. Q is a moiety containing a free electron pair positioned three to six atoms from the $C(=Y_2)$ moiety. In a preferred embodiment, the free electron pair is five atoms from this oxygen. Q can be selected from the non-limiting list of $C_{2-4}$ alkyls or cycloalkyls, aryls or aralkyl groups substituted with a member of the group consisting of O, S and $NR_{12}$, wherein $R_{12}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls. The free electron pair can be anywhere along the Q moiety as long as the defined spacing between the free electron pair and the oxygen is maintained.

In these embodiments, $R_{11}$ is attached to Q via $N(R_{12})$, O, or S. Thus, Q assists hydrolysis of the prodrug linkage by anchimeric assistance because the free electron pair moiety can generate a three- to six-membered, but preferably five-membered, ring by-product upon hydrolysis of the preferably ester linkage.

Q can also be selected from the group consisting of $C_{2-4}$ alkyls, cycloalkyls, aryls, aralkyl groups substituted with a member of the group consisting of NH, O, S, $—CH_2—C(=O)—NH—$, and ortho-substituted phenyls such as

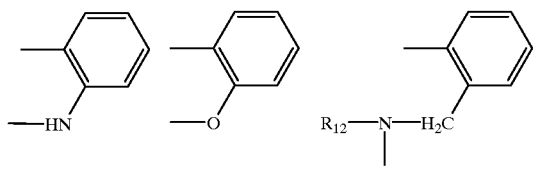

3. Drug Generation Via Hydrolysis of the Prodrug

The prodrug compounds of the present invention are designed so that the $T_{1/2}$ circulation is greater than the $T_{2+ee}$ hydrolysis, i.e. $T_{+e,fra\ 2+ee}$ circulation$>T_{+e,fra\ 1/2}$ hydrolysis in plasma.

The linkages included in the compounds have a $T_{1/2}$ hydrolysis in the plasma of the mammal being treated which is short enough to allow sufficient amounts of the parent compounds, i.e. the amino-containing bioactive compound, to be released prior to elimination. Some preferred compounds of the present invention, i.e. those in which (n) is 1, have plasma $T_{1/2}$ hydrolysis rates ranging from about 5 minutes to about 12 hours. Preferably, the compositions have a plasma $T_{1/2}$ hydrolysis ranging from about 0.5 to about 6 hours and most preferably from about 1 to about 4 hours.

4. Trialkyl Lock Facilitated Lactonization Native Drug Regeneration

Once the double prodrug ester hydolysis has taken the place, the resultant second prodrug moiety remains. According to the present invention, this prodrug entity will undergo a further independent reaction in vivo to produce the desired native compound. This reaction occurs relatively immediately after the ester hydrolysis occurs and is a trialkyl lock lactonization reaction initiated by simple proton removal of the phenolic intermediate which causes the following cyclization which then releases the amine-containing parent compound. The reaction is shown below.

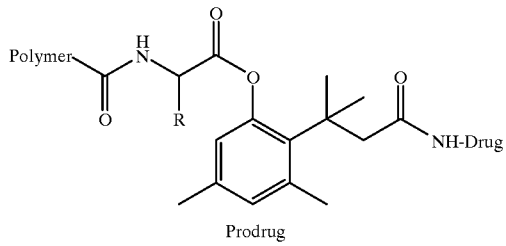
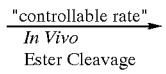
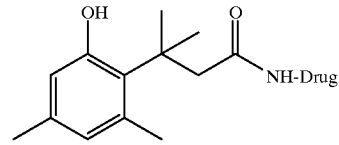

Prodrug

"controllable rate"
*In Vivo*
Ester Cleavage

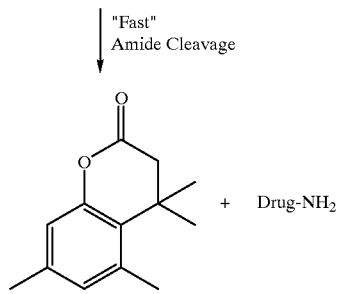

"Fast"
Amide Cleavage

+ Drug-NH$_2$

Final Product

D. Substantially Non-Antigenic Polymers

The "double prodrug" compositions of the present invention include a water-soluble polymer, $R_{11}$.

In preferred aspects of the invention, $R_{11}$ includes a capping group A which can be hydrogen, $C_{1-6}$ alkyl moieties, carboxyalkyl, dialkyl acyl urea alkyls, or a compound of formula (II) shown below.

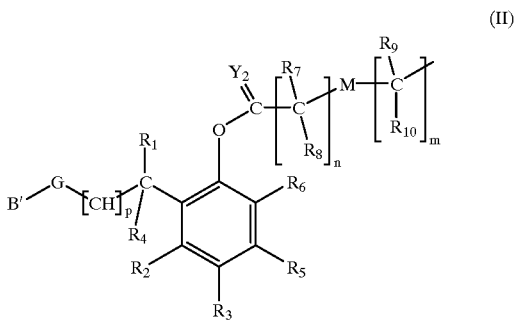

(II)

wherein B' is the same as B or another member of the group defined by B and the remaining variables are as set forth above with regard to Formula (I).

Suitable examples of such polymers include polyalkylene oxides such as polyethylene glycols which are also preferably substantially non-antigenic. The general formula for PEG and its derivatives, i.e. A'—O—(CH$_2$CH$_2$O)$_x$—(CH$_2$)$_n$—A, where (x) represents the degree of polymerization (i.e. 10–2,300) or number of repeating units in the polymer chain and is dependent on the molecular weight of the polymer, (n) is zero or a positive integer, A is a capping group as defined herein, i.e. an —H, amino, carboxy, halo, $C_{1-6}$ alkyl or other activating group and A' is the same as A or another A moiety. Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998"; the disclosure of each is incorporated herein by reference. It will be understood that the water-soluble polymer will be functionalized for attachment to the linkage via M, X or Q herein. As an example, the PEG portion of the prodrugs can be the following non-limiting compounds: —C(=Y)—(CH$_2$)$_n$—O—(CH$_2$CH$_2$O)$_x$—A, —C(=Y)—Y—(CH$_2$)$_n$—O—(CH$_2$CH$_2$O)$_x$—A and —C(=Y)—NR$_{12}$—(CH$_2$), —O—(CH$_2$CH$_2$O)$_x$—A, where Y is O or S and $R_{12}$, (n) and (x) are as defined above.

In particular, polyethylene glycols (PEG's), mono-activated, $C_{1-4}$ alkyl-terminated PAO's such as mono-methyl-terminated polyethylene glycols (mPEG's) are preferred when mono-substituted polymers are desired; bis-activated polyethylene oxides are preferred when disubstituted prodrugs are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting mPEG-OH to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in molecular weight, polymers ranging from about 2,000 to about 100,000 are usually selected for the purposes of the present invention. Molecular weights of from about 5,000 to about 50,000 are preferred and 5,000 to about 40,000 are particularly preferred. The molecular weight of the polymer selected for inclusion in the "double prodrug" must be sufficient so as to provide sufficient circulation of the "double prodrug" before hydrolysis of the linker. Within the ranges provided above, polymers having molecular weight ranges of at least 20,000 are preferred for chemotherapeutic and organic moieties. In the case of nucleophiles such as proteins, enzymes and the like, polymers having a molecular weight range of from about 2,000 to about 20,000 are preferred.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immune response in mammals.

E. The Polymeric Double Prodrug Transport System

The double prodrugs of the present invention can be prepared in at least two fashions. One technique schematically shown in FIG. 1, includes a. providing an intermediate compound (III)

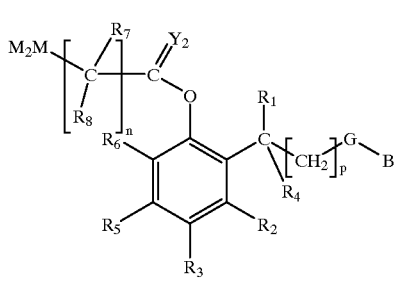

(III)

where $M_2$ is a cleavable or reversible protecting group and all other variables are as set forth above with regard to Formula (I);

b. treating the intermediate compound (III) with a strong acid such as TFA (trifluoroacetic acid) or other trihaloacetic acid, HCl, sulfuric acid, etc., or catalytic hydrogenation to remove the protecting group; and c. reacting the unprotected intermediate compound (III) with a moiety capable of reacting with an M such as an activated polymer, i.e. a polymer having a reactive functional group, e.g., p-nitrophenyl or succinimidyl carbonate, carbonyl imidazole, thiazolidine thione or the like, to form an activated double prodrug transport form of formula (IV):

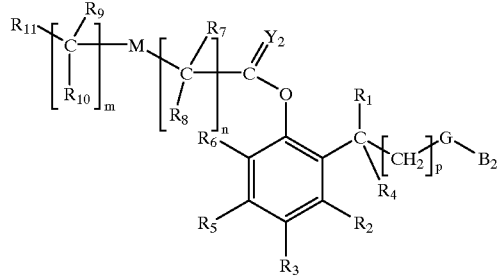

(IV)

where $B_2$ is a leaving group (i.e. same as B) and all other variables are as set forth above with regard to Formula (I); and optionally d. attaching the parent amine-containing compound to the compound (IV)

Figure 2:
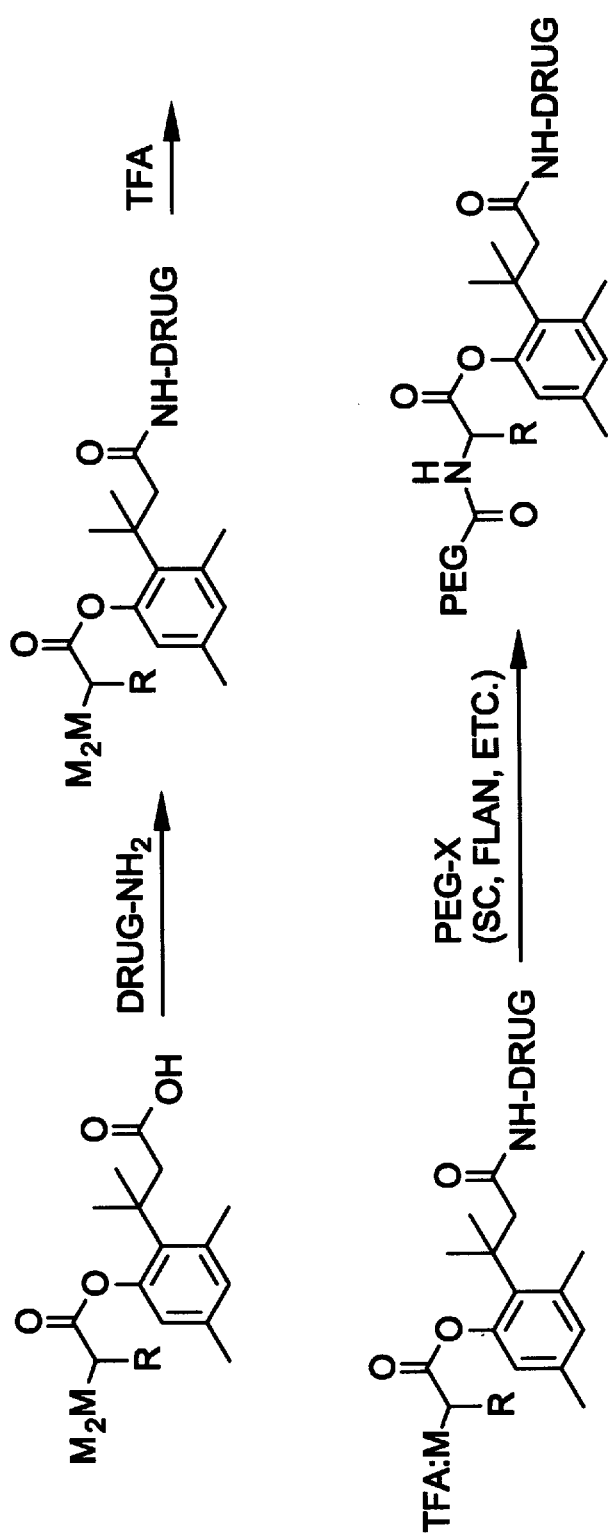
Figure 3:
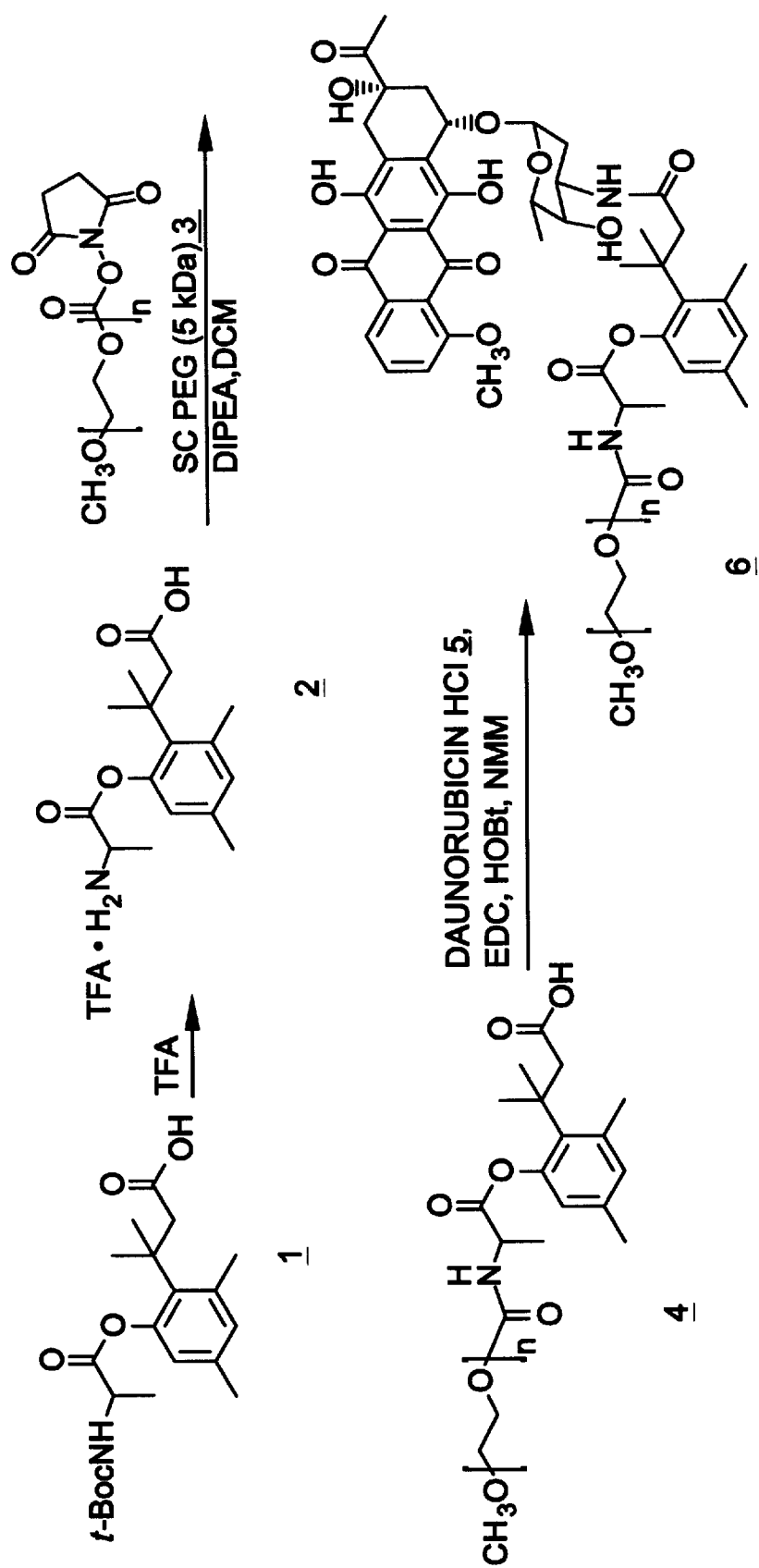
FIG. 3 illustrates the reaction schemes associated with Examples 1–3.

Alternatively, as shown in FIG. 2, the transport form (PEG-prodrug) can be prepared by:

a. attaching the parent amine-containing compound to the intermediate compound (III);

b. removing the protecting group; and c. reacting the unprotected intermediate with an activated polymer to form the activated double prodrug.

Intermediate compound (III) can be prepared using standard organic synthesis techniques. For example, blocked dialkylphenyl propionic acid derivatives such as 3-(2'-Boc-alanyl-4',4'-dimethylphenyl)-3,3-dimethylpropionic acid can be synthesized using a procedure disclosed by Binghe Wang, et al. Synthesis of a Novel Esterase-Sensitive Cyclic Prodrug System for Peptides That Utilizes a "Trimethyl Lock"—Facilitated Lactonization Reaction. *J. Org. Chem.* 1997, 62, 1363.), the disclosure of which is incorporated herein by reference.

Attachment of the parent compound to intermediate compound (III) or (IV) can be carried out using standard organic synthesis techniques using coupling agents known to those of ordinary skill in the art such as 1,3-diisopropylcarbodiimide (DIPC), dialkyl carbodiimides, 2-halo-1-alkyl-pyridinium halides, 1-(3-dimethylaminopropyl)-3-ethyl carbodiimide (EDC), propane phosphonic acid cyclic anhydride (PPACA) and phenyl dichlorophosphates. Alternatively, when B is a good leaving group such as those listed below in F.1., a coupling agent is not required and the reaction proceeds in the presence of a base.

Removal of the protecting group is carried out in the same manner as described in the first method.

F. The Leaving Group or Residue Portion "B"

1. Leaving Groups

In those aspects where B is a leaving group, suitable leaving groups include, without limitations, moieties such as N-hydroxybenzotriazolyl, halogen, N-hydroxyphthalimidyl, p-nitrophenoxy, imidazolyl, N-hydroxysuccinimidyl; thiazolidinyl thione, or other good leaving groups as will be apparent to those of ordinary skill.

The leaving groups are attached to the benzyl portion of the compound after the "double" prodrug portion, i.e. the PEG portion has been formed. The synthesis reactions used and described herein will be understood by those of ordinary skill without undue experimentation. For purposes of illustration and not limitation, generally, the activated forms of the double prodrug transport system are prepared by acylating the phenolic hydroxy of a compound of formula (V) below:

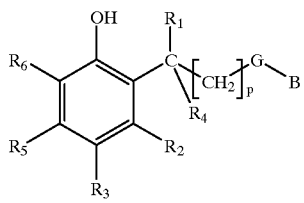

wherein:

$R_{1-6}$, (p), G, and B are as set forth above in regard to Formula (I); and thereafter reacting the acylated resultant compound with an activating group for coupling to a target, e.g., compounds such as 4-nitrophenyl-chloroformate, disuccinimidyl carbonate (DSC), carbonyldiimidazole, thiazolidine thione, etc. to provide the desired derivative.

Once in place, the "activated" form of the PEG prodrug is ready for conjugation with an amine-containing compound. Some preferred activated transport forms are shown below:

a.

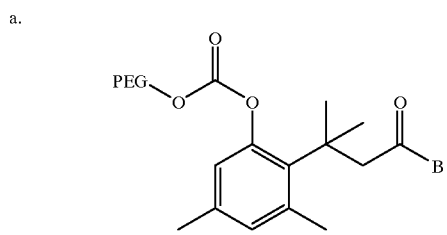

b.

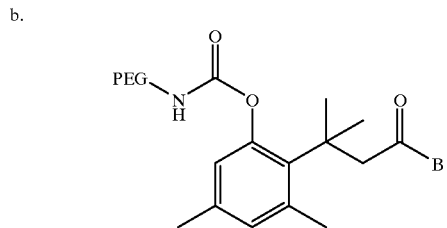

c.

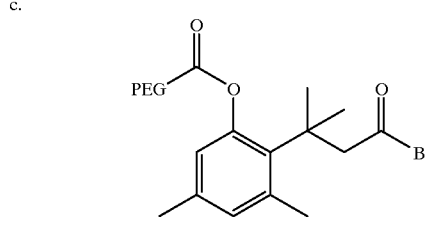

d.

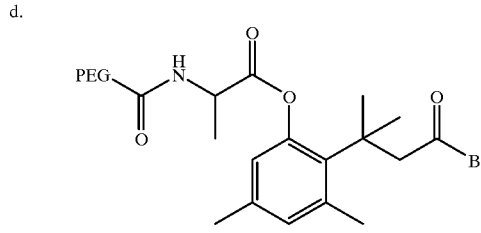

-continued e.

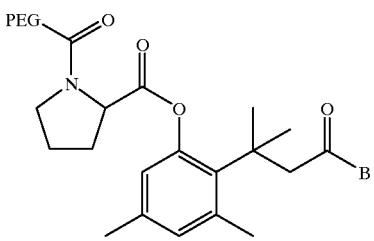

f.

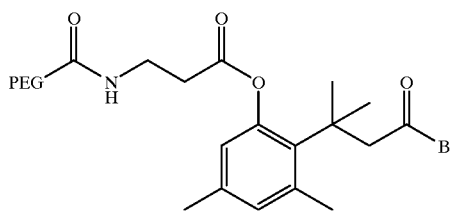

g.

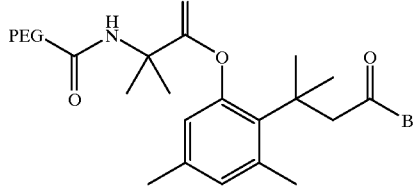

h.

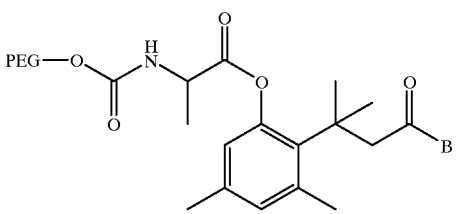

2. Residues of Amine-containing Compounds

In those aspects of the invention where B is a residue of an amine-containing compound, a non-limiting list of such suitable compounds include residues of organic compounds, enzymes, proteins, polypeptides, etc. Organic compounds include, without limitation, moieties such as anthracycline compounds including daunorubicin, doxorubicin; p-aminoaniline mustard, Ara-C or cytosine arabinoside and related compounds, gemcitabine, etc. Alternatively, B can be a residue of an amine-containing cardiovascular agent, anti-neoplastic, anti-infective, anti-fungal such as nystatin and amphotericin B, anti-anxiety agent, gastrointestinal agent, central nervous system-activating agent, analgesic, fertility agent, contraceptive agent, anti-inflammatory agent, steroidal agent, anti-urecemic agent, vasodilating agent, vasoconstricting agent, etc.

Suitable proteins, polypeptides, enzymes, peptides and the like having at least one available amino group for polymer attachment include materials which have physiological or pharmacological activities as well as those which are able to catalyze reactions in organic solvents. The only other requirement of the amine-containing materials is that they maintain at least some portion of the activity associated with the unmodified protein, enzyme, peptide, etc. after the prodrug transport portion has hydrolyzed.

Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, α-, β- and γ-interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related proteins, growth factors such as transforming growth factors, such as TGFα's or TGFβ's and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Also included herein is any portion of a polypeptide demonstrating in vivo bioactivity. This includes amino acid sequences, nucleic acids (DNA, RNA), peptide nucleic acids (PNA), antibody fragments, single chain binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like. The foregoing is illustrative of the proteins which are suitable for the present invention. It is to be understood that those proteins, as defined herein, not specifically mentioned but having an available amino group are also intended and are within the scope of the present invention.

In a preferred aspect of the invention, the amino-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds can be similarly modified without undue experimentation. It is to be understood that those biologically active materials not specifically mentioned but having suitable amino-groups are also intended and are within the scope of the present invention.

The only limitations on the types of amino-containing molecules suitable for inclusion herein is that there is available at least one (primary or secondary) amine containing position which can react and link with a carrier portion and that there is not substantial loss of bioactivity after the double prodrug system releases and regenerates the parent compound.

It is noted that parent compounds suitable for incorporation into the double prodrug compositions of the invention, may themselves be substances/compounds which are not active after hydrolytic release from the linked composition, but which will become active after undergoing a further chemical process/reaction. For example, an anticancer drug that is delivered to the bloodstream by the double prodrug transport system, may remain inactive until entering a cancer or tumor cell, whereupon it is activated by the cancer or tumor cell chemistry, e.g., by an enzymatic reaction unique to that cell.

After conjugation, the remaining amine-containing compound is referred to as the residue of the unconjugated compound.

3. Polymeric Hybrids

In another aspect of the invention there are provided hybrid types of the polymeric double prodrug system described herein. In particular, the hybrid system includes not only the reversible double prodrug system but also a second polymeric system based on more permanent types of linkages. The hybrids can be prepared by at least two methods. For example, the trialkyl lock-based double prodrug protein conjugate can be first synthesized, and then PEGylated using any art-recognized activated polymer such as thiazolidine thione or succinimidyl carbonate-activated PEG. Alternatively, the more permanent conjugation reaction can be performed first (i.e. the parent compound is PEGylated) and the resultant conjugates can be used to form the trialkyl lock double prodrug conjugates described herein. It will be understood that the hybrid systems will be better suited for proteins, enzymes and the like where multiple amino groups are available for attachment of the polymeric amino prodrug. For purposes of the present invention, "activated polymers" will be understood to include polymers containing one or more terminal groups which are capable of reacting with one or more of α-amino groups, ε-amino groups, histidine nitrogens, carboxyl groups, sulfhydryl groups, etc. found on enzymes, proteins, etc., as well as such groups found on synthetically prepared organic compounds.

The activating terminal moiety can be any group which facilitates conjugation of the polymers with the biologically active material, i.e. protein, enzyme, etc. either before of after the double prodrug transport system of the present invention has been synthesized. See, for example, U.S. Pat. No. 4,179,337, the disclosure of which is hereby incorporated by reference. Such activating groups can be a moiety selected from:

I. Functional groups capable of reacting with an amino group such as:
   a) carbonates such as the p-nitrophenyl, or succinimidyl; see, for example, U.S. Pat. No. 5,122,614, the disclosure of which is hereby incorporated by reference;
   b) carbonyl imidazole;
   c) azlactones; see, for example, U.S. Pat. No. 5,321,095, the disclosure of which is hereby incorporated by reference;

d) cyclic imide thiones see, for example, U.S. Pat. No. 5,349,001, the disclosure of which is hereby incorporated by reference; or
e) isocyanates or isothiocyanates.
f) active esters such as N-hydroxy-succinimidyl or N-hydroxybenzotriazolyl.

II. Functional groups capable of reacting with carboxylic acid groups and reactive carbonyl groups such as:
a) primary amines, or
b) hydrazine and hydrazide functional groups such as the acyl hydrazides, carbazates, semicarbamates, thiocarbazates, etc.

III. Functional groups capable of reacting with mercapto or sulfhydryl groups such as maleimides; see, for example, Shearwater Polymers Catalog "Polyethylene Glycol Derivatives 1997–1998", the disclosure of which is hereby incorporated by reference;

IV. Functional groups capable of reacting with hydroxyl groups such as (carboxylic) acids or other nucleophiles capable of reacting with an electrophilic center, such as isocyanate, activated esters or carbonates, cyclic imides, thiones, etc.

The activating moiety can also include a spacer moiety located proximal to the polymer. The spacer moiety may be a heteroalkyl, alkoxy, alkyl containing up to 18 carbon atoms or even an additional polymer chain. The spacer moieties can added using standard synthesis techniques.

F. Synthesis of Double Prodrugs

Synthesis of specific prodrugs is set forth in the Examples. Generally, however, the double prodrugs of the invention are preferably prepared either by reacting the activated transport form described above as compound (IV) with the parent compound in the presence of a coupling agent such as DIPC, EDC, DMAP phenyldichlorophosphate, etc. or base, if required (see FIG. 1) or attaching the parent compound to the intermediate compound (formula III) and thereafter reacting the resultant compound with an activated polymer as schematically shown in FIG. 2. In either case, the resulting conjugated double prodrug composition is then recovered or isolated using techniques known to those of ordinary skill, i.e. filtered, recrystallized.

Preferably the substituents are reacted in an inert solvent such as methylene chloride, chloroform, toluene, DMF or mixtures thereof. The reaction also preferably is conducted in the presence of a base, such as dimethylaminopyridine, diisopropylethylamine, pyridine, triethylamine, etc. to neutralize any acids generated and at a temperature from 0° C. up to about 22° C. (room temperature).

G. Methods of Treatment

Another aspect of the present invention provides methods of treatment for various medical conditions in mammals. The methods include administering to the mammal in need of such treatment, an effective amount of a composition of the invention, as described herein, such as a double prodrug of doxorubicin The prodrug compositions are useful for, among other things, treating diseases which are similar to those which are treated with the parent compound, e.g. enzyme replacement therapy, neoplastic disease, reducing tumor burden, preventing metastasis of neoplasms and preventing recurrences of tumor/neoplastic growths in mammals.

The amount of the prodrug that is administered will depend upon the amount of the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, double prodrug polymeric derivatives of nitrogen mustard derivatives are administered in amounts ranging from about 5 to about 500 mg/m$^2$ per day. The range set forth above is illustrative and those skilled in the art will determine the optimal dosing of the prodrug selected based on clinical experience and the treatment indication. Actual dosages will be apparent to the artisan without undue experimentation.

The compositions, including prodrugs, of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof.

H. EXAMPLES

The following examples serve to provide further appreciation of the invention but are not meant in any way to restrict the effective scope of the invention. The underlined and bold-faced numbers recited in the Examples correspond to those shown in the Figures.

Example 1

Compound 2

Trifluoroacetic Acid Salt of Alanine Ester of 3-(2'-Hydroxy-4',6'-dimethylphenyl)-3,3-dimethylpropionic Acid 1 g (2.54 mmol) of t-Boc-alanine ester of 3-(2'-hydroxy-4',6'-dimethylphenyl)-3,3-dimethylpropionic acid, 1 (synthesized using the procedure of *J. Org. Chem.* 1997, 62, 1363.), was stirred in 20 mL of TFA-CH$_2$Cl$_2$ (1:1, v/v) at room temperature for 2 hours. The solvent was removed in vacuo and ether was added to the residue to precipitate 2 (0.6873 g, 67%).

$^1$H NMR (270 MHz, CDCl$_3$) δ 1.41 (3H, s, C(C$\underline{H}_3$)$_2$), 1.42 (3H, s, C(C$\underline{H}_3$)$_2$), 1.54 (3H, d, J=8.1 Hz, C$\underline{H}$—CH$_3$), 2.21 (3H, s, Ar—C$\underline{H}_3$), 2.45 (3H, s, Ar—C$\underline{H}_3$), 2.65 (2H, s, C$\underline{H}_2$COOH), 4.36 (1H, d, J=8.1 Hz, C$\underline{H}$—CH$_3$), 6.57 (1H, s, Ar—H), 6.81 (1H, s, Ar—H).

$^{13}$C NMR (67.80 MHz, CDCl$_3$) δ 15.27 (Ar—$\underline{C}$H$_3$), 19.57 (Ar—$\underline{C}$H$_3$), 24.66 ($\underline{C}$HCH$_3$), 30.92 (C($\underline{C}$H$_3$)$_2$), 38.28 ($\underline{C}$H$_2$COOH), 47.32 ($\underline{C}$(CH$_3$)$_2$), 48.45 ($\underline{C}$HCH$_3$), 122.23, 132.30, 133.97, 135.61, 138.05, 149.10 (Ar), 169.50 (—$\underline{C}$OOAr), 172.50 ($\underline{C}$OOH).

Example 2

Compound 4

Coupling of 2 with SC PEG (5 kDa), 3

2 g (0.39 mmol) of succinimidyl carbonate-activated PEG (SC PEG) (5 kDa), prepared as shown in commonly assigned U.S. Pat. No. 5,122,614, the contents of which are incorporated herein by reference, 3, was added to the mixture of 175.8 mg (0.6 mmol) of 2 and 280 µL (1.5 mmol) of N,N-diisopropyl-ethylamine (DIPEA) in 40 mL of anhydrous dichloromethane. The reaction mixture was stirred at room temperature overnight. The solvent was removed and the product was crystallized from 80 mL of 2-propanol to give 1.86 g (93%) of 4 as a white solid.

$^{13}$C NMR (67.80 MHz, CDCl$_3$) δ 16.01 (Ar—$\underline{C}$H$_3$), 18.94 (Ar—$\underline{C}$H$_3$), 24.07 ($\underline{C}$HCH$_3$), 30.11 (C($\underline{C}$H$_3$)$_2$), 30.20 (C($\underline{C}$H$_3$)$_2$), 37.49 ($\underline{C}$H$_2$COOH), 46.04 ($\underline{C}$(CH$_3$)$_2$), 49.11 ($\underline{C}$HCH$_3$), 57.59 (O$\underline{C}$H$_3$), 62.86–70.68 (PEG), 121.37, 131.04, 132.80, 134.54, 136.71, 148.62 (Ar), 154.80 (O$\underline{C}$(=O)NH), 170.82 (—$\underline{C}$OOAr), 171.27 ($\underline{C}$OOH).

Example 3

Compound 6
Coupling of 4 with Daunorubicin Hydrochloride, 5

8.4 mg (0.2 mmol) of EDC was added to the mixture of 0.5 g (0.1 mmol) of 4, 84.6 mg (0.15 mmol) of daunorubicin hydrochloride, 5, 40.4 mg (0.4 mmol) of N-methylmorpholine, and 20.3 mg (0.2 mmol) of 1-hydroxybenzotriazole hydrate in 10 mL of anhydrous dichloromethane at 0° C. The reaction mixture was stirred at room temperature overnight and filtered. The filtrate was concentrated in vacuo and the residue was recrystallized from 20 mL of 2-propanol to give 0.44 g (88%) of 6. UV assay showed 0.7 equivalent (70% of coupling yield) of daunorubicin.

$^{13}$C NMR (67.80 MHz, CDCl$_3$) δ 15.66, 15.81, 18.96, 23.56, 24.45, 29.96, 30.78, 30.84, 32.32, 33.65, 38.61, 44.13, 17.78, 49.45, 55.48, 57.73, 63.17–75.35 (PEG), 99.79, 109.81, 109.94, 117.75, 117.80, 118.37, 119.26, 121.45, 131.39, 133.02, 133.21, 133.92, 134.74, 134.78, 134.85, 135.04, 137.30, 148.88, 154.36, 155.17, 155.41, 159.84, 169.36, 171.81, 185.14, 185.33, 210.58.

Example 4

Compound 8
Coupling of 2 with mPEG (5 kDa) Thazolidine Thione, 7

0.5 g (0.1 mmol) of mPEG (5 kDa) thiazolidine thione, prepared as disclosed in commonly-assigned U.S. Pat. No. 5,349,001, the contents of which are incorporated herein by reference, 7 was added to the mixture of 44 mg (0.15 mmol) of 2 and 70 µL (0.4 mmol) of DIPEA in 10 mL of anhydrous dichloromethane at room temperature. The mixture was stirred at room temperature overnight. Solvent was removed under reduced pressure and the residue was recrystallized from 2-propanol to give 0.44 g (88%) of product as a white solid.

$^{13}$C NMR (67.80 MHz, CDCl$_3$) δ 16.22, 19.17, 24.29, 30.37, 37.71, 46.37, 47.29, 57.85, 67.40–72.38 (PEG), 121.58, 131.38, 132.95, 134.85, 136.99, 148.75, 169.08, 170.53, 171.50.

Example 5

Compound 9
Coupling of 8 with Daunorubicin Hydrochloride, 5

39 mg (0.2 mmol) of EDC is added to the mixture of 0.5 g (0.1 mmol) of 8, 85 mg (0.15 mmol) of daunorubicin hydrochloride, 5, 40 mg (0.4 mmol) of N-methylmorpholine, and 20 mg (0.2 mmol) of 1-hydroxybenzotriazole hydrate in 10 mL of anhydrous dichloromethane at 0° C. The reaction mixture is stirred at room temperature overnight and filtered. The filtrate is concentrated in vacuo and the residue recrystallized from 20 mL of 2-propanol to give 0.45 g (90%) of 9.

Example 6

Compound 11
Coupling of 2 with PEG (40 kDa) Dithiazolidine Thione, 10

1 g (0.025 mmol) of PEG (40 kDa) dithiazolidine thione, 10, was added to the mixture of 29 mg (0.099 mmol) of 2 and 36.6 µL (0.20 mmol) of DIPEA in 15 mL of anhydrous dichloromethane. The mixture was stirred at room temperature overnight. The solvent was removed under reduced pressure and the residue was recrystallized from 2-propanol to give 0.8 g (80%) of 11 as a white solid.

$^{13}$C NMR (67.80 MHz, CDCl$_3$) δ 16.90, 19.48, 24.45, 30.81, 38.34, 46.83, 47.87, 68.52–72.82 (PEG), 76.19, 77.83, 122.00, 131.77, 133.76, 135.40, 137.51, 149.46, 169.28, 170.88, 171.55.

Example 7

Compound 12
Coupling of 11 with Daunorubicin Hydrochloride, 5

94.5 mg (0.492 mmol) of EDC was added to the mixture of 2.5 g (0.0615 mmol) of 11 (40 kDa), 208 mg (0.3688 mmol) of daunorubicin hydrochloride, 5, 99.4 mg (0.984 mmol) of N-methylmorpholine, and 49.8 mg (0.369 mmol) of 1-hydroxybenzotriazole hydrate in 50 mL of anhydrous dichloromethane at 0° C. The reaction mixture was stirred at room temperature overnight and filtered. The filtrate was concentrated in vacuo and the residue was recrystallized from 2-propanol (200 mL) to give 2.3 g (92%) of 12. UV assay showed 1.9 equivalents (95% of coupling yield) of daunorubicin.

$^{13}$C NMR (67.80 MHz, CDCl$_3$) δ 16.14, 19.31, 23.55, 24.63, 28.80, 31.15, 32.78, 34.77, 39.23, 44.97, 48.12, 56.18, 66.80–75.95 (PEG), 100.14, 110.93, 118.68, 119.13, 121.81, 131.88, 133.86, 134.02, 134.96, 135.03, 137.96, 149.56, 155.20, 160.73, 169.73, 170.22, 171.34, 186.05, 210.41.

Example 8

Compound 14
Coupling of 11 with p-Amino-(N,N-di-2-chloroethyl)aniline hydrochloride, 13

37.8 mg (0.20 mmol) of EDC was added to the mixture of 1.0 g (0.025 mmol) of 11 (40 kDa), 39.8 mg (0.15 mmol) of p-amino-(N,N-di-2-chloroethyl)aniline hydrochloride, 13 (synthesized using a modified procedure of Edwards et al. Cytotoxic Compounds. Part XVII. o-, m-, and p-(Bis-2-chloroethylamino)phenol, p-[N-(2-Chloethyl)methylamino] phenol, N,N-Bis-2-chloroethyl-p-phenylenediamine, and N,N-Bis-2-chloroethyl-N'-methyl-p-phenylenediamine as Sources of Biologically Active Carbamates. *JCS Perkin I*, 1973, 2397.), 39.7 mg (0.39 mmol) of N-methylmorpholine, and 19.9 mg (0.15 mmol) of 1-hydroxybenzotriazole hydrate in 20 mL of anhydrous dichloromethane at 0° C. The reaction mixture was stirred at room temperature overnight and filtered. The filtrate was concentrated in vacuo and the residue was recrystallized from 2-propanol (100 mL) to give 0.8 g (80%) of 14. A UV assay showed 1.5 equivalents (75% of coupling yield) of the aromatic nitrogen mustard.

$^{13}$C NMR (67.80 MHz, CDCl$_3$) δ 15.63, 19.35, 24.86, 30.99, 31.10, 39.12, 39.81, 47.99, 48.36, 52.84, 67.79–71.79 (PEG), 111.59, 120.97, 121.57, 129.04, 131.86, 133.83, 135.38, 137.93, 141.53, 149.12, 168.37, 170.25, 171.66.

Example 9

Compound 15
Coupling of 11 with 2-Mercaptothiazoline 5 g (0.12 mmol) of 11 is azeotroped in 70 mL of toluene by distillation of 20 mL of toluene for 2 hours. The solution is cooled to 35° C. and 60 μL (0.63 mmol) of oxalyl chloride and 5 μL of DMF added. The solution is stirred at 35–40° C. for 3 hours followed by addition of 89.5 mg (0.75 mmol) of 2-mercaptothiazoline and 60 μL (0.75 mmol) of N,N-diisopropylethylamine. The mixture is refluxed overnight and concentrated in vacuo. The residue is recrystallized from 250 mL of 2-propanol to give 15 as a white solid.

Example 10

Compound 17
Coupling of 15 with Ara-C, 16

A solution of 1 g (0.025 mmol) of 15, 24 mg (0.1 mmol) of Ara-C, 16 (Purchased from Sigma Chemical Co., St. Louis, Mo.), and 24 mg (0.2 mmol) of DMAP in 15 mL of anhydrous methylene chloride is refluxed overnight. The solvent is removed in vacuo and the residue is recrystallized from 80 mL of 2-propanol to give of 17, as a colorless solid.

Example 11

Compound 18
Coupling of 8 with N-Hydroxysuccinimide 2.5 g (0.47 mmol) of 8 and 108 mg (0.94 mmol) of N-hydroxysuccinimide were dissolved in 40 mL of anhydrous dichloromethane at 0° C. 114 mg (0.94 mmol) of DMAP and 118 mg (0.94 mmol) of DIPC were added to the mixture. The reaction mixture was stirred overnight at ambient temperature. The solvent was removed in vacuo and the residue was recrystallized from 2-propanol to give 2.1 g (84%) of 18 as a white solid.

$^{13}$C NMR (67.80 MHz, CDCl$_3$) δ 16.38, 19.46, 24.47, 24.75, 30.11, 30.36, 38.21, 43.66, 47.58, 58.12, 67.97–71.13 (PEG), 121.81, 131.80, 131.93, 135.68, 137.01, 148.89, 165.87, 168.55, 169.34, 171.03.

Example 12

Compound 20
Conjugation of 18 to (L)-Asparaginase 450 mg (0.083 mmol, 317 eqiv.) of PEG linker, 18, is added to 37.5 mg (416 μL, 0.00027 mmol) of native (L)-asparaginase, 19, in 3 mL of sodium phosphate buffer (0.1 M, pH 7.8) with gentle stirring. The solution is stirred at 30° C. for 30 minutes. A GPC column (Zorbax GF-450) is used to monitor PEG conjugation: The PEG-Asp conjugate has a retention time of 8.5 minutes. At the end of the reaction (as evidenced by the absence of native enzyme), the mixture was diluted with 12 mL of formulation buffer (0.05 M sodium phosphate, 0.85% sodium chloride, pH 7.3) and diafiltered with a Centriprep concentrator (Amicon) having a molecular weight cut-off 50,000 daltons to remove the unreacted PEG. Diafiltration is continued as needed at 4° C. until no more free PEG is detected by mixing equal amount of filtrate and 0.1% PMA (polymethacrylic acid in 0.1 M HCl).

The product, 20, is not stable in basic buffer solution for prolonged periods of time, therefore the solution is lyophilized and 20 is stored in the freezer (−20° C.). After 15 days of storage in this manner, GPC analysis indicates less than 0.8% decomposition. The specific activity of freshly prepared 20 is found to be 137 IU/mg (native asparaginase= 217 IU/mg). Protein modification of asparaginase with SS-PEG (a permanent linker) using a procedure corresponding to that described in the aforementioned U.S. Pat. No. 4,179,337 gives a similar activity of 120 IU/mg. A TNBS assay is used to calculate the percentage modification of the protein, and the Biuret assay is used to check the protein concentration.

Example 13
Kinetics of Hydrolysis of 20 in Rat Plasma and Buffer

The rate of hydrolysis of 20 in rat plasma is measured using a GPC column (Zorbax GF-450) and is found to have a half life of <2 hours. The half life in phosphate buffer (pH 7.4) is determined to be much greater than 2 hours.

Example 14

Compound 20A
A Protein Hybrid—Conjugation of 20 with SS-PEG (a permanent linker)

393 mg (0.073 mmol, 70 equiv.) of 18 is reacted with 150 mg (1.664 mL, 0.00106 mmol) of native (L)-asparaginase, 19, in 30 mL of sodium phosphate buffer (0.1 M, pH 7.8) as described in Example 13 at 30° C. for 15 minutes to provide a solution of 20, followed by the addition of 1.272 g (0.245 mmol, 230 equiv.) of SS-PEG. The reaction solution is stirred for another 15 minutes. The pH of the reaction mixture is maintained at 7.8 with 0.5 M sodium hydroxide. The reaction mixture is diluted with 30 mL of sterile water and diafiltered using a Centriprep concentrator (Amicon) having a molecular weight cut-off of 50,000 Daltons to remove any unreacted PEG. Diafiltration is continued as needed at 4° C. until no more free PEG is detected by mixing equal amount of filtrate and 0.1% PMA (polymethacrylic acid in 0.1 M HCl). A GPC column (Zorbax GF-450) is used to follow the course of the reaction. The final solution of product, 20A, is lyophilized and stored in the freezer.

Example 15

Compound 20B
Demonstration of Selective Removal of Reversible PEG Linker from the Hybrid, 20A—Generation of a Permanently Modified Asparaginase, 20B 100 mg of hybrid linker modified asparaginase, 20A, is dissolved in 30 mL of pH 7.8 phosphate buffer and stirred at 30° C. overnight. This solution is diluted with 30 mL of sterile water, and diafiltered with a Centriprep concentrator (Amicon) having a molecular weight cut off of 50,000 Daltons to remove the free PEG which is formed by selective cleavage of the conjugated from reversible PEG linker, 8. The solution now contains only SS-PEG conjugated asparaginase, 20B. Thus the reversible linker is hydrolyzed, leaving only the relatively permanently bonded PEG attached to asparaginase.

Example 16

Compound 22
t-Boc-Proline Ester of 1-O-t-Butyldimethylsilyl-3-(2'-hydroxy-4',6'-Dimethylphenyl)-3,3-dimethylpropanol, 21

392 mg (3.11 mmol) of DIPC was added to a mixture of 0.5 g (1.55 mmol) of 1-O-t-Butyldimethylsilyl-3-(2'-hydroxy-4',6'-Dimethylphenyl)-3,3-dimethylpropanol, 21 (synthesized using the procedure of R. T. Borchardt, et al. Amine Prodrugs Which Utilize Hydroxy Amide Lactonization. II. A Potential Esterase-Sensitive Amide Prodrug. *Pharm. Res.* 1991, 8, 455), 568 mg (4.66 mmol) of DMAP, and 668 mg (3.11 mmol) of t-Boc-Proline-OH in 15 mL of anhydrous dichloromethane at 0° C. The mixture was stirred at room temperature overnight, filtered, and concentrated. The residue was purified by column chromatography on silica gel (ethyl acetate-hexane 3:7, v/v) to give 700 mg (87%) of 22.

$^1$H NMR (270 MHz, CDCl$_3$) δ 0.04, (s, 3H, C$\underline{H}_3$—Si), 0.14 (s, 3H, C$\underline{H}_3$—Si), 0.88 (s, 3H, C$\underline{H}_3$—C), 0.92 (s, 3H, C$\underline{H}_3$—C), 1.51 (s, 9H, Si(C$\underline{H}_3$)$_3$), 1.55 (s, 9H, C(C$\underline{H}_3$)$_3$), 2.00 (m, 2H, C$\underline{H}_2$O), 2.07 (t, 2H, CH$_2$C$\underline{H}_2$CH$_2$, J=8.1 Hz), 2.25 (s, 3H, PhC$\underline{H}_3$), 2.30 (m, 2H, CHC$\underline{H}_2$) 2.55 (s, 3H, PhC $\underline{H}_3$), 3.53 (t, 2H, C$\underline{H}_2$N, J=8.1 Hz), 4.57 (bs, 1H, COC$\underline{H}$N), 6.65 (bs, 1H, Ph$\underline{H}$), 6.82 (s, 1H, Ph$\underline{H}$).

$^{13}$C NMR (67.80 MHz, CDCl$_3$) δ 18.23, 20.06, 25.14, 25.70, 25.98, 28.49, 32.00, 32.06, 39.51, 46.24, 46.62, 59.74, 60.93, 80.08, 122.73, 132.14, 134.56, 135.87, 138.30, 150.68, 171.84.

Example 17

Compound 23 t-Boc-Proline Ester of 3-(2'-hydroxy-4',6'-Dimethylphenyl)-3,3-dimethylpropanol

A solution of 2.82 g (5.43 mmol) of 22 in 10 mL of tetrahydrofuran, 10 mL of H$_2$O and 30 mL of glacial acetic acid was stirred at room temperature for 1 hour. The solvent was removed in vacuo to give a crude product 23 as a colorless oil, which was carried to the next step without further purification.

$^1$H NMR (270 MHz, CDCl$_3$) δ 0.01, 0.77, 0.84, 1.38, 1.40, 1.42, 1.93, 1.97, 2.01, 2.13, 2.38, 2.43, 3.47, 4.48, 6.50, 6.70.

$^{13}$C NMR (67.80 MHz, CDCl$_3$) δ −3.71, 19.95, 20.29, 23.19, 25.06, 25.20, 25.59, 28.44, 31.78, 32.04, 32.27, 33.21, 39.33, 42.96, 46.01, 46.53, 46.62, 59.62, 60.22, 64.95, 66.59, 80.44, 103.87, 122.59, 132.04, 132.27, 134.23, 135.79, 135.89, 138.14, 150.37, 150.55, 154.52, 171.86, 175.10.

Example 18

Compound 24

Oxidation of 3-(2'-hydroxy-4',6'-Dimethylphenyl)-3,3-dimethylpropanol, 23

A solution of 2.5 g (6.2 mmol) of 23 in 125 mL of anhydrous methylene chloride was added to a solution of 2.88 g (13.4 mmol) of pyridinium chlorochromate (PCC) in 125 mL of anhydrous methylene chloride. The mixture was stirred at room temperature for 1 hour followed by filtration through Celite. The solvent was removed in vacuo and the residue was purified by silica gel column chromatography (ethyl acetate/hexane=3:7, v/v). The product aldehyde, was dissolved in 25 mL of acetone and added to a solution of 1 g (6.3 mmol) of KMnO$_4$ in 25 mL of acetone-H$_2$O (1:1, v/v). The mixture was stirred at room temperature overnight. 40 mL of H$_2$O was added and acetone was removed in vacuo before filtration through Celite. The aqueous solution was adjusted to pH=3.0 with 1N HCl, followed by extraction with ethyl acetate (30 mL×2). Solvent was removed under reduced pressure and hexane was added to precipitate 24 (550 mg, 21% from 23).

$^1$H NMR (270 MHz, CDCl$_3$) δ 1.41, 1.46, 1.50, 1.52, 1.61, 1.97, 2.21, 2.30, 2.33, 2.54, 2.85, 3.56, 4.56, 6.57, 6.79.

$^{13}$C NMR (67.80 MHz, CDCl$_3$) δ 20.09, 24.13, 25.17, 28.14, 28.56, 29.87, 31.40, 31.57, 39.12, 46.79, 47.40, 59.76, 80.68, 122.56, 132.43, 134.04, 136.27, 138.29, 150.21, 171.87.

Example 19

Compound 25

Trifluoroacetic Acid Salt of Proline Ester of 3-(2'-hydroxy-4',6'-Dimethylphenyl)-3,3-dimethylpropionic Acid 0.55 g (1.31 mmol) of t-Boc-proline ester of 3-(2'-hydroxy-4',4'-dimethylphenyl)-3,3-dimethylpropionic acid, 24, was stirred in 10 mL of TFA-CH$_2$Cl$_2$ (1:1, v/v) at room temperature for 1 hour. Solvent was removed completely in vacuo to give 25 as a yellow foamy solid (0.436 g, 77%).

$^1$H NMR (270 MHz, CDCl$_3$) δ 1.53, 1.55, 2.03, 2.19, 2.48, 2.59, 2.76, 3.32, 4.61, 6.54, 6.85, 9.80.

$^{13}$C NMR (67.80 MHz, CDCl$_3$) δ 13.86, 23.73, 24.86, 28.27, 31.70, 31.92, 38.99, 46.43, 47.76, 60.33, 122.25, 133.08, 133.74, 136.65, 138.89, 149.30, 168.35.

Example 20

Compound 26

Coupling of 25 with PEG (40 kDa) Dithiazolidine Thione, 10

52.6 mg (0.41 mmol) of DIPEA was added to the solution of 65 mg (0.15 mmol) of 25 and 1 g (0.025 mmol) of 10 in 15 mL of anhydrous dichloromethane. The mixture was stirred at room temperature overnight. The solvent was removed in vacuo and the residue was recrystallized from 2-propanol to give 0.85 g (85%) of 26 as a white solid.

$^{13}$C NMR (67.80 MHz, CDCl$_3$) δ 19.61, 24.39, 27.34, 30.72, 38.11, 45.86, 59.13, 68.40–71.45 (PEG), 122.18, 131.78, 133.40, 135.04, 137.18, 149.36, 168.65, 170.67, 171.18.

Example 21

Compound 27

Coupling of 26 with Daunorubicin Hydrochloride, 5

13.2 mg (0.07 mmol) of EDC was added to the mixture of 0.35 g (0.01 mmol) of 26, 29 mg (0.05 mmol) of 5, 13.9 mg (0.14 mmol) of N-methylmorpholine, and 6.97 mg (0.05 mmol) of 1-hydroxybenzotriazole hydrate in 20 mL of anhydrous dichloromethane at 0° C. The reaction mixture was stirred at room temperature overnight and filtered. The filtrate was concentrated in vacuo and the residue was recrystallized from 2-propanol (50 mL) to give 0.35 g (84%) of 27. UV assay showed 2.0 equivalents (100% of coupling yield) of daunorubicin.

Example 22

Compound 29

Compound 28 was prepared using the procedure provided in Example 16. Thus 500 mg (1.55 mmol) of 21, 587.6 mg (3.11 mmol) of t-Boc-β-alanine-OH, 474 μL (3.11 mmol) of DIPC, and 568 mg (4.66 mmol) of DMAP in 15 mL of anhydrous dichloromethane were reacted to give 580 mg (76%) of 28.

$^1$H NMR (270 MHz, CDCl$_3$) δ 0.00 (s, 6H, 2×C$\underline{H}_3$—Si), 0.87 (s, 6H, 2×C$\underline{H}_3$—C), 1.48 (s, 18H, C(C$\underline{H}_3$)$_3$ and Si(C $\underline{H}_3$)$_3$), 2.05 (t, 2H, C$\underline{H}_2$C, J=5.4Hz), 2.26 (s, 3H, PhC$\underline{H}_3$), 2.54 (s, 3H, PhC$\underline{H}_3$), 2.79 (t, 2H, C$\underline{H}_2$C(=O), J=5.4 Hz), 3.50 (t, 4H, NHC$\underline{H}_2$ and C$\underline{H}_2$O, J=8.1 Hz), 5.01 (bs, 1H, N $\underline{H}$), 6.58 (s, 1H, Ph$\underline{H}$), 6.84 (s, 1H, Ph$\underline{H}$).

$^{13}$C NMR (67.80 MHz, CDCl$_3$) δ 18.18, 20.11, 25.20, 25.88, 28.36, 31.78, 35.40, 36.00, 38.99, 45.94, 60.69, 79.35, 122.91, 132.38, 13 3.99, 135.92, 138.40, 149.46, 155.79, 171.73.

Compound 29 is prepared using the same procedure as described for the conversion of 22 into 27 (Examples 17–21).

Example 23

Compound 31

Compound 30 was prepared using the procedure given in Example 16. Compound 21, 150 mg (0.47 mmol), 189.4 mg (0.93 mmol) oft-Boc-α-aminoisobutyric acid, 117.4 mg (0.93 mmol) of DIPC, and 113.7 mg (0.93 mmol) of DMAP in 25 mL of anhydrous dichloromethane were reacted and after purification, 76 mg (32%) of 30 was obtained.

$^1$H NMR (270 MHz, CDCl$_3$) δ 0.00 (s, 6H, 2×C$\underline{H}_3$—Si), 0.87 (s, 6H, 2×C$\underline{H}_3$—C), 1.48 (s, 18H, C(C$\underline{H}_3$)$_3$ and Si(C$\underline{H}_3$)$_3$), 1.70 (s, 6H, C(C$\underline{H}_3$)$_2$), 2.06 (t, 2H, C$\underline{H}_2$C, J=8.1 Hz), 2.19 (s, 3H, PhC$\underline{H}_3$), 2.54 (s, 3H, PhC$\underline{H}_3$), 3.50 (t, 2H, C$\underline{H}_2$O, J=8.1 Hz), 5.19 (bs, 1H, N$\underline{H}$), 6.70 (s, 1H, Ph$\underline{H}$), 6.81 (s, 1H, Ph$\underline{H}$).

$^{13}$C NMR (67.80 MHz, CDCl$_3$) δ 18.16, 50.13, 25.17, 25.33, 25.90, 28.33, 31.92, 32.04, 39.28, 45.08, 45.83, 56.44, 60.80, 61.61, 79.96, 116.65, 122.70, 126.74, 132.17, 134.12, 136.07, 138.04, 151.07, 154.70, 174.24.

Compound 30 is subjected to the procedures of Examples 17–21 to obtain compound 31.

The various publications, patents, patent applications and published applications mentioned in this application are hereby incorporated by reference herein.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:

1. A compound comprising the formula:

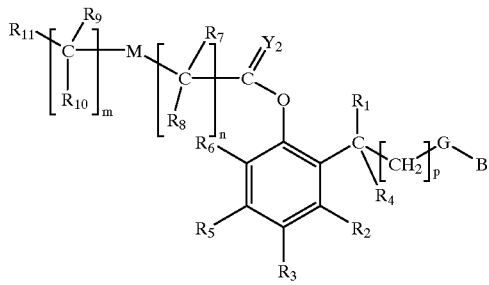

(I)

wherein:

B is H, OH, OSiR$_{13}$ or a residue of an amine-containing target moiety;

G is

or CH$_2$;

Y$_{1-2}$ are independently O or S;

M is X or Q;

X is an electron withdrawing group;

Q is a moiety containing a free electron pair positioned three to six atoms from C(=Y$_2$);

R$_1$, R$_4$, R$_7$, R$_8$, R$_9$, R$_{10}$ and R$_{13}$ are independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls and substituted C$_{1-6}$ heteroalkyls;

R$_2$, R$_3$, R$_5$ and R$_6$ are independently selected from the group consisting of hydrogen, C$_{1-6}$ alkyls, C$_{1-6}$ alkoxy, phenoxy, C$_{1-8}$ heteroalkyls, C$_{1-8}$ heteroalkoxy, substituted C$_{1-6}$ alkyls, C$_{3-8}$ cycloalkyls, C$_{3-8}$ substituted cycloalkyls, aralkyls, aryls, substituted aryls, such as aryls substituted with halo-, nitro- and cyano-; carboxy-, C$_{1-6}$ carboxyalkyls and C$_{1-6}$ alkyl carbonyls;

(m) is zero or one;

(n) is zero or a positive integer;

(p) is zero, one or two; and

R$_{11}$ is a substantially non-antigenic polymer.

2. The compound of claim 1, wherein R$_2$ and R$_5$ are C$_{1-6}$ alkyls.

3. The compound of claim 1, wherein R$_2$ and R$_5$ are methyl.

4. The compound of claim 1, wherein R$_3$ and R$_6$ are hydrogen.

5. The compound of claim 1, wherein R$_{11}$ further comprises a capping group A.

6. The compound of claim 5, wherein A is selected from the group consisting of hydrogen, CO$_2$H, C$_{1-6}$ alkyl moieties, dialkyl acyl urea alkyls and

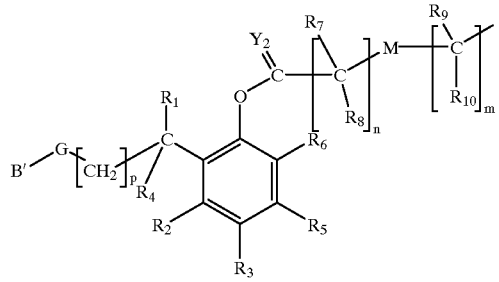

wherein B' is the same as B or another member of the group defined as B.

7. The compound of claim 1, wherein R$_1$ and R$_4$ are independently selected from the group consisting of hydrogen, CH$_3$ and CH$_2$CH$_3$.

8. The compound of claim 1, wherein said substituted C$_{1-6}$ alkyl is selected from the group consisting of carboxyalkyls, aminoalkyls, dialkylaminos, hydroxyalkyls and mercaptoalkyls.

9. The compound of claim 1, wherein X is selected from the group consisting of O, NR$_{12}$, S, SO and SO$_2$, where R$_{12}$ is selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls and substituted C$_{1-6}$ heteroalkyls.

10. The compound of claim 9, wherein X is selected from the group consisting of O and NR$_{12}$.

11. The compound of claim 1, wherein Q is selected from the group consisting of C$_{2-4}$ alkyls, cycloalkyls, aryls, aralkyl groups substituted with a member of the group consisting of NH, O, S, —CH$_2$—C(O)—NH—, and ortho-substituted phenyls.

12. The compound of claim 1, wherein (n) is an integer from 1 to about 12.

13. The compound of claim 12, wherein (n) is 1 or 2.

14. The compound of claim 1, wherein (m) is 0.

15. The compound of claim 1, wherein (p) is one.

16. The compound of claim 1, wherein Y$_{1-2}$ are O.

17. The compound of claim 1, wherein R$_{11}$ comprises a polyalkylene oxide.

18. The compound of claim 17, wherein said polyalkylene oxide comprises polyethylene glycol.

19. The compound of claim 1 wherein said polymer has a molecular weight of from about 2,000 to about 100,000.

20. The compound of claim 19, wherein said polymer has a molecular weight of from about 5,000 to about 40,000.

21. The compound of claim 1, wherein $R_{11}$ is selected from the group consisting of $-C(=Y)-(CH_2)_n-O-(CH_2CH_2O)_x-A$, $-C(=Y)-Y-(CH_2)_n-O-(CH_2CH_2O)_x-A$ and $-C(=Y)-NR_{12}-(CH_2)_n-O-(CH_2CH_2O)_x-A$, where $R_1$ and $R_4$ are independently selected from the group consisting of hydrogen, $C_{1-6}$ alkyls, $C_{1-6}$ heteroalkyls, substituted $C_{1-6}$ heteroalkyls and substituted $C_{1-6}$ alkyls;

(n) is zero or a positive integer;

Y is O or S,=;

A is a capping group; and (x) represents the degree of polymerization.

22. The compound of claim 1 wherein B is a leaving group selected from the group consisting of N-hydroxybenzotriazolyl, halogen, N-hydroxyphthalimidyl, p-nitrophenoxy, imidazolyl, N-hydroxysuccinimidyl, thiazolidinyl thione, or an acid activating group.

23. The compound of claim 1 wherein B is a residue of a member of the group consisting of anthracyclines, daunorubicin, doxorubicin, p-hydroxyaniline mustard, Ara-C, cytosine arabinoside and gemcitabine.

24. The compound of claim 1, wherein B is a residue of an enzyme, protein, peptide or an amine containing compound selected from the group consisting of cardiovascular agents, anti-neoplastics, anti-infectives, anti-fungals, anti-anxiety agents, gastrointestinal agents, central nervous system-activating agents, analgesics, fertility agents, contraceptive agents, anti-inflammatory agents, steroidal agents, anti-urecemic agents, vasodilating agents, and vasoconstricting agents.

25. The compound of claim 1, wherein B includes a second polymeric transport system.

26. A compound of claim 1, selected from the group consisting of:

a. 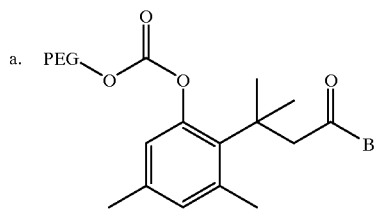

b. 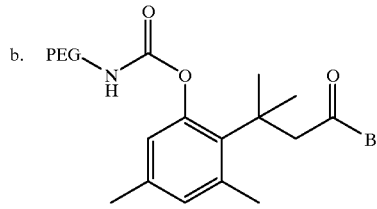

c. 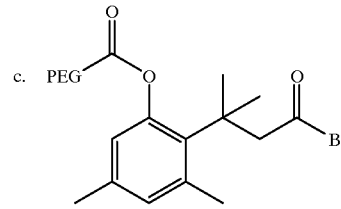

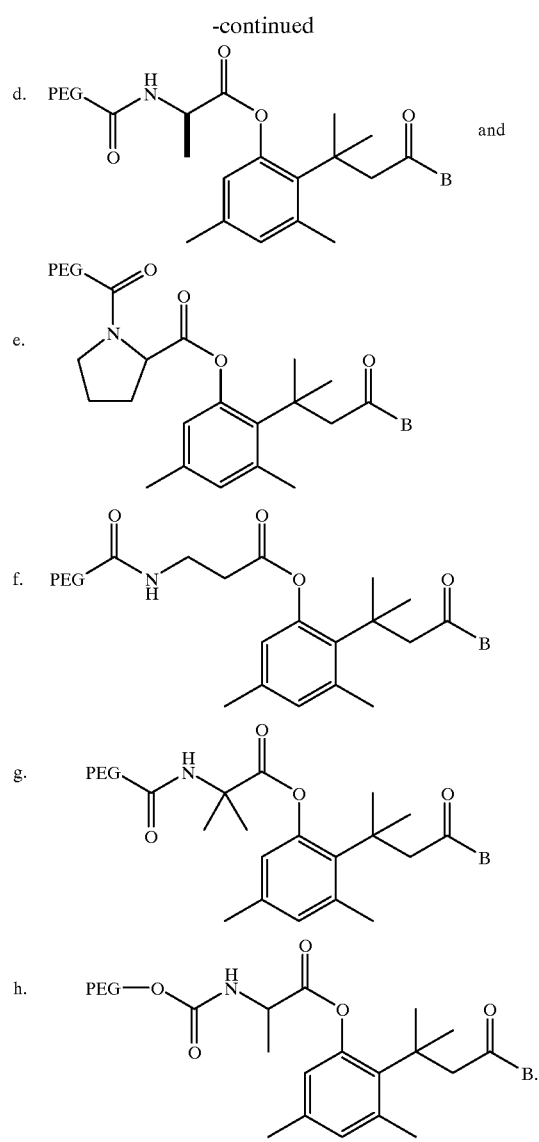

27. A method for preparing a trialkyl lock based prodrug transport form, comprising:

a. providing an intermediate compound (III)

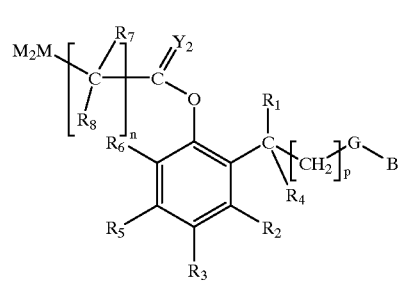

(III)

where $M_2$ is a cleavable or reversible protecting group

B is H, OH, $OSiR_{13}$ or a residue of an amine-containing target moiety;

27

G is

or $CH_2$;

$Y_{1-2}$ are independently O or S;

M is X or Q;

X is an electron withdrawing group;

Q is a moiety containing a free electron pair positioned three to six atoms from $C(=Y_2)$;

$R_1$, $R_4$, $R_7$, $R_8$, and $R_{13}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aralkyls, aryls, substituted aryls, such as aryls substituted with halo-, nitro- and cyano-; carboxy-, $C_{1-6}$ carboxyalkyls and $C_{1-6}$ alkyl carbonyls;

(n) is zero or a positive integer;

(p) is zero, one or two; and b. treating the intermediate compound (III) with an acid; and c. reacting the unprotected intermediate with a compound capable of reacting with an M and forming a compound of Formula (IV):

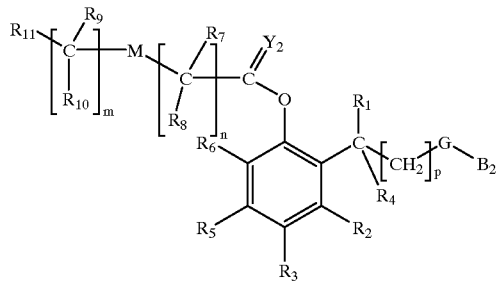

(IV)

where $B_2$ is a leaving group;

$R_9$, and $R_{10}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

$R_{11}$ is a substantially non-antigenic polymer; and all other variables are as set forth above.

28. A method for preparing a trialkyl lock based prodrug transport form, comprising:

28 a. providing an intermediate compound (III)

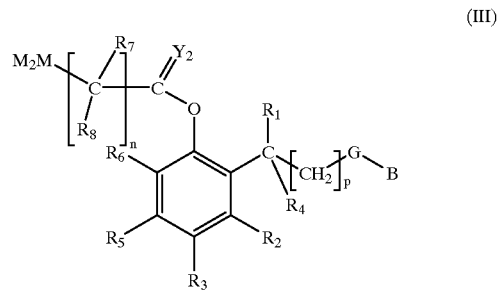

(III)

where $M_2$ is a cleavable or reversible protecting group

B is H, OH, $OSiR_{13}$ or a residue of an amine-containing target moiety;

G is

or $CH_2$;

$Y_{1-2}$ are independently O or S;

M is X or Q;

X is an electron withdrawing group;

Q is a moiety containing a free electron pair positioned three to six atoms from $C(=Y_2)$;

$R_1$, $R_4$, $R_7$, $R_8$, and $R_{13}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

$R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aralkyls, aryls, substituted aryls, such as aryls substituted with halo-, nitro- and cyano-; carboxy-, $C_{1-6}$ carboxyalkyls and $C_{1-6}$ alkyl carbonyls;

(n) is zero or a positive integer;

(p) is zero, one or two; and b. coupling the intermediate compound (III) to an amine-containing compound to form a trialkyl lock-based intermediate;

c. deprotecting the trialkyl lock-based intermediate with an acid; and d. reacting the unprotected trialkyl lock-based intermediate intermediate with an activated polymer to form a compound of the formula(I):

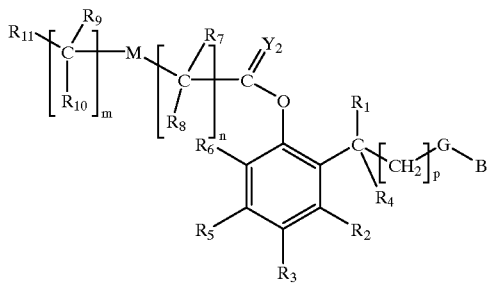 (I)

$R_9$, $R_{10}$, are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

$R_{11}$ is a substantially non-antigenic polymer; and all other variables are as set forth above.

29. The method of claim 28, further comprising reacting the compound of formula (I) with an activated polymer to form a hybrid transport system.

30. A method of treating a mammal with prodrugs, comprising:

administering to a mammal in need of such treatment an effective amount of a compound of claim 1.

31. The compound of claim 25, wherein B includes an attachment moiety for said second polymeric transport system selected from the group consisting of alpha amino, epsilon amino, histidine nitrogen, carboxyl, reactive carbonyl, mercapto, sulfhydryl and hydroxyl.

32. The compound of claim 25, wherein B is a member of the group consisting of proteins, polypeptides, peptides and enzymes.

33. The compound of claim 32, wherein said B is a cytokine or an interferon.

34. The compound of claim 33, wherein said cytokine is an interleukin.

35. The compound of claim 34, wherein said interleukin is selected from the group consisting of IL-1 to IL-13.

36. The compound of claim 33, wherein said interferon is selected from the group consisting of α-interferons, β-interferons, and γ-interferons.

37. The method of claim 29, wherein said activated polymer forming said hybrid system includes a moiety selected from the group consisting of p-nitrophenyl carbonate, succinimidyl carbonate, carbonyl imidazole, azlactone, cyclic imide thione, isocyanate, isothiocyanate, primary amine, hydrazine, acyl hydrazide, cabazate, semicarbazate, thiocarbazate, phenyl glyoxal, carboxylic acid, and nucleophiles capable of reacting with an electrophilic center.

38. The method of claim 29, wherein B is a member of the group consisting of proteins, polypeptides, peptides and enzymes.

39. The method of claim 38, wherein said B is a cytokine or an interferon.

40. The method of claim 39, wherein said cytokine is an interleukin.

41. The method of claim 39, wherein said interleukin is selected from the group consisting of IL-1 to IL-13.

42. The method of claim 39, wherein said interferon is selected from the group consisting of α-interferons, β-interferons, and γ-interferons.

* * * * *

UNITED STATES PATENT AND TRADEMARK OFFICE
CERTIFICATE OF CORRECTION

PATENT NO. : 5,965,119
DATED : October 12, 1999
INVENTOR(S) : GREENWALD, et al.

Figure 4:
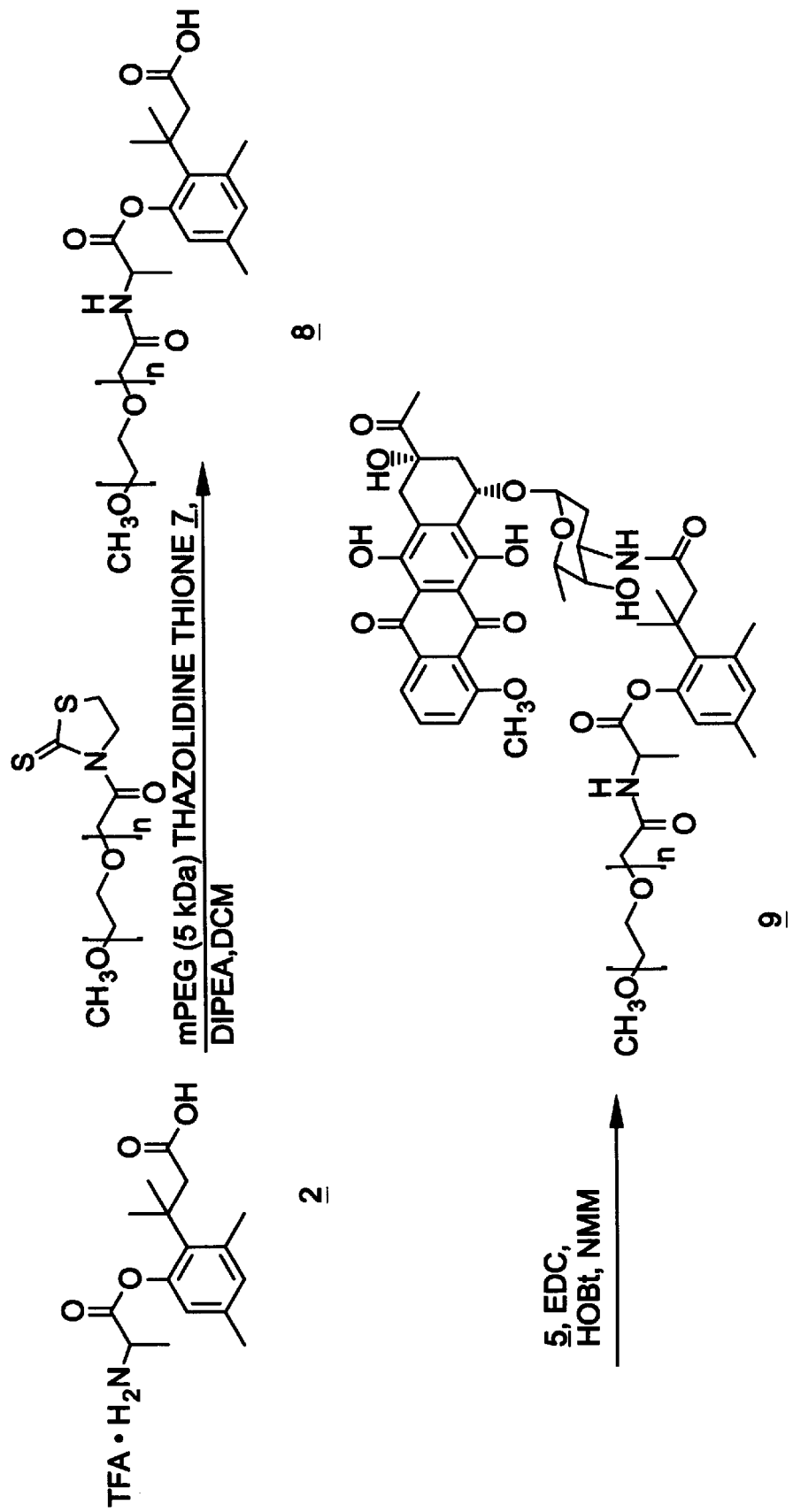
FIG. 4 illustrates the reaction schemes associated with Examples 4–5.
Figure 5:
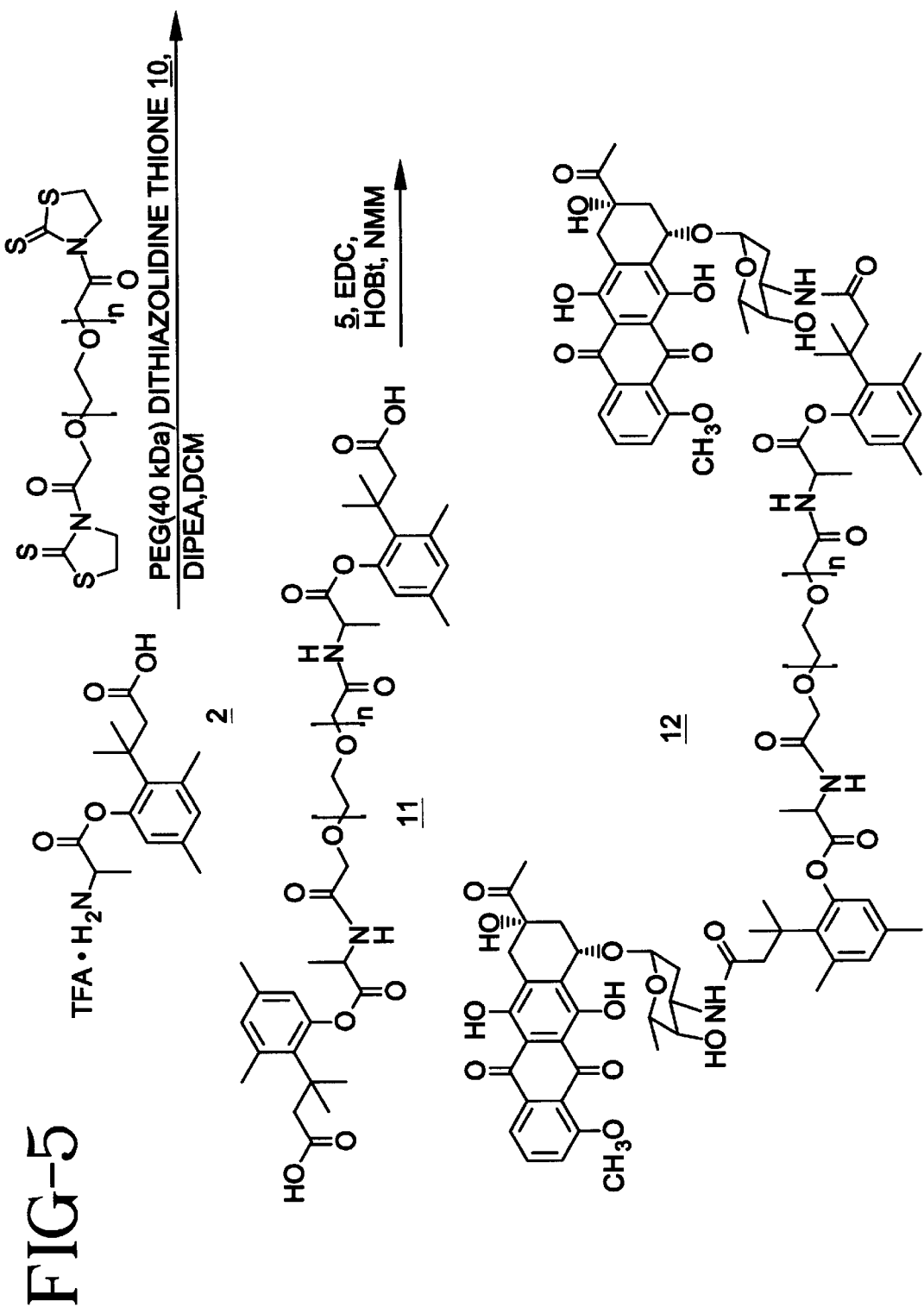
FIG. 5 illustrates the reaction schemes associated with Examples 6–7.
Figure 6:
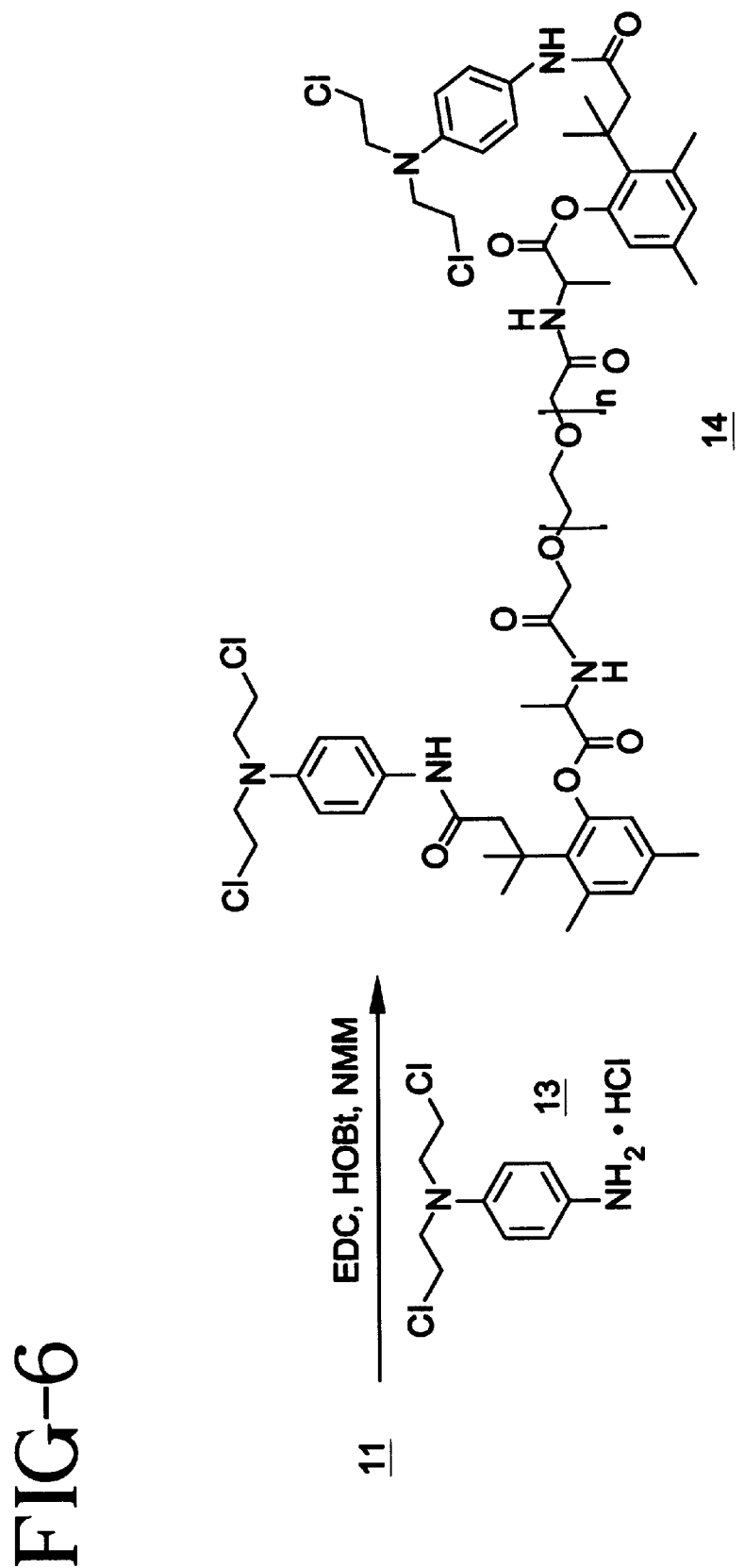
FIG. 6 illustrates the reaction scheme associated with Example 8.
Figure 7:
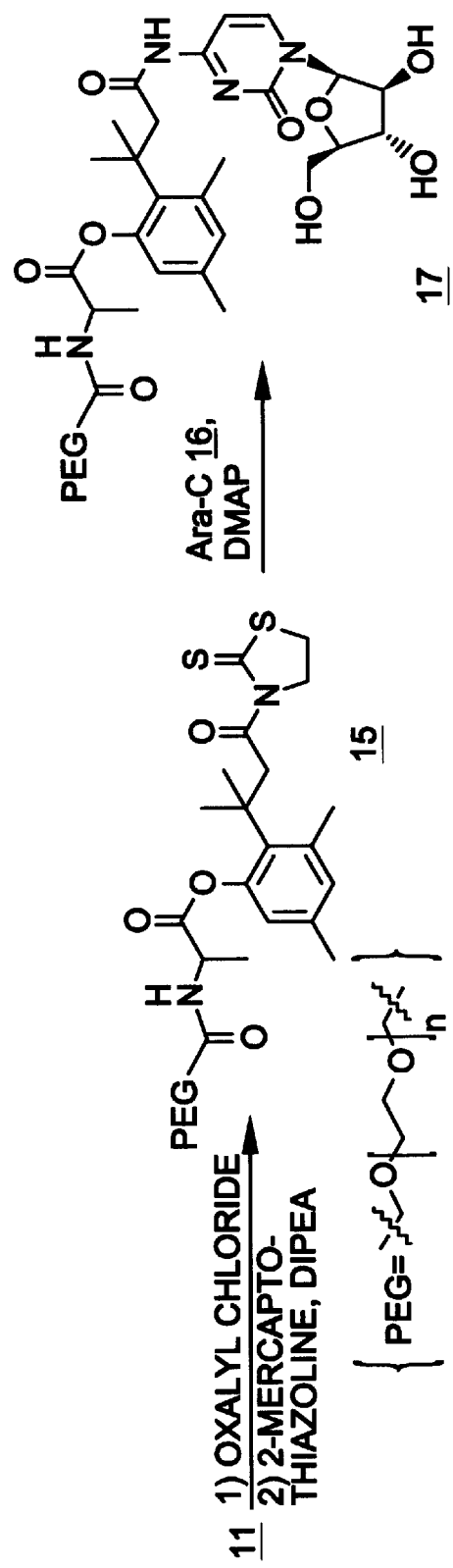
FIG. 7 illustrates the reaction schemes associated with Examples 9–10.
Figure 8:
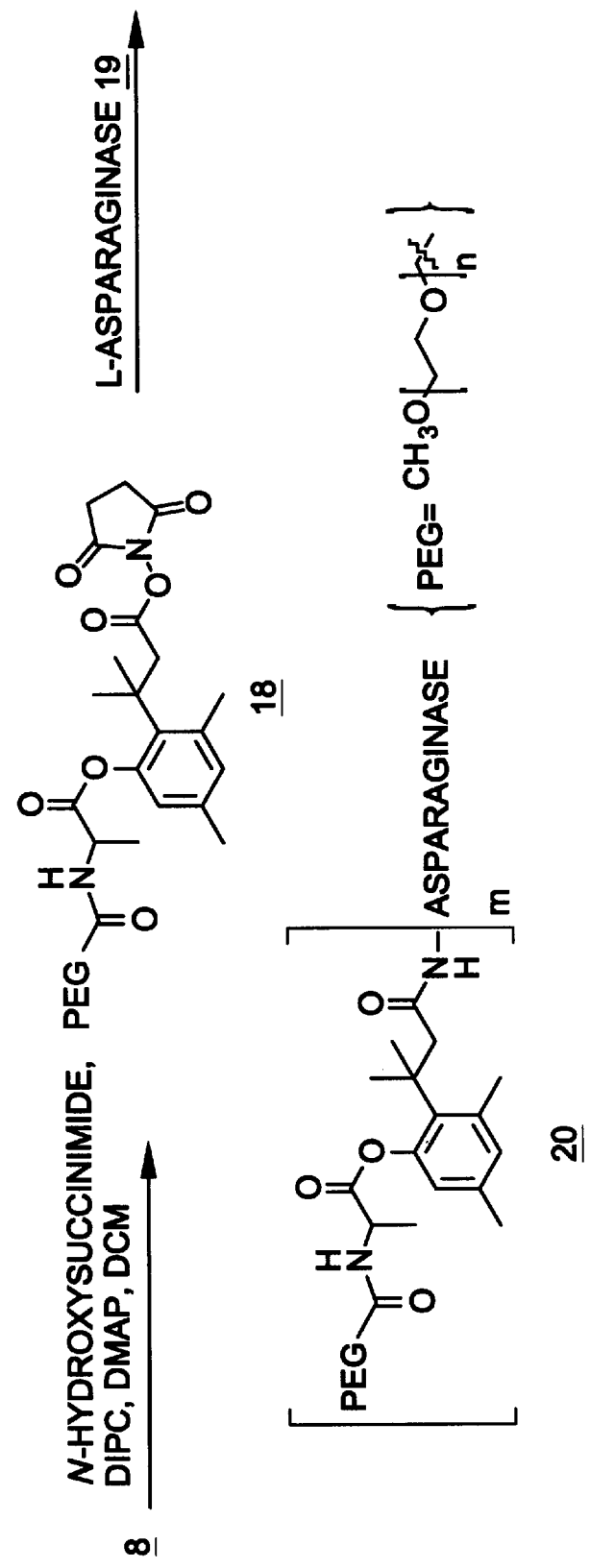
FIG. 8 illustrates the reaction schemes associated with Examples 11–12.
Figure 9:
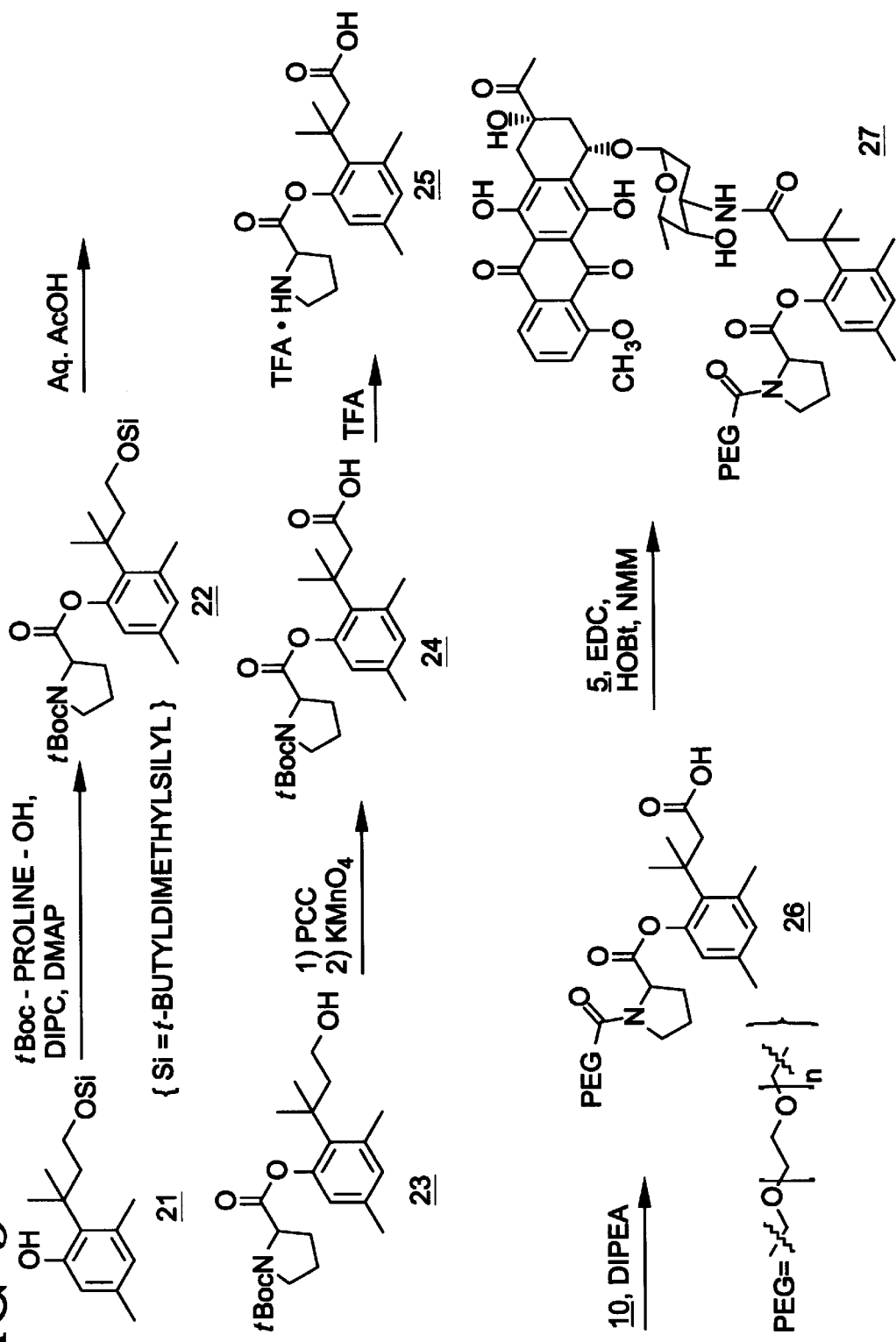
FIG. 9 illustrates the reaction schemes associated with Example 16–21.
Figure 10:
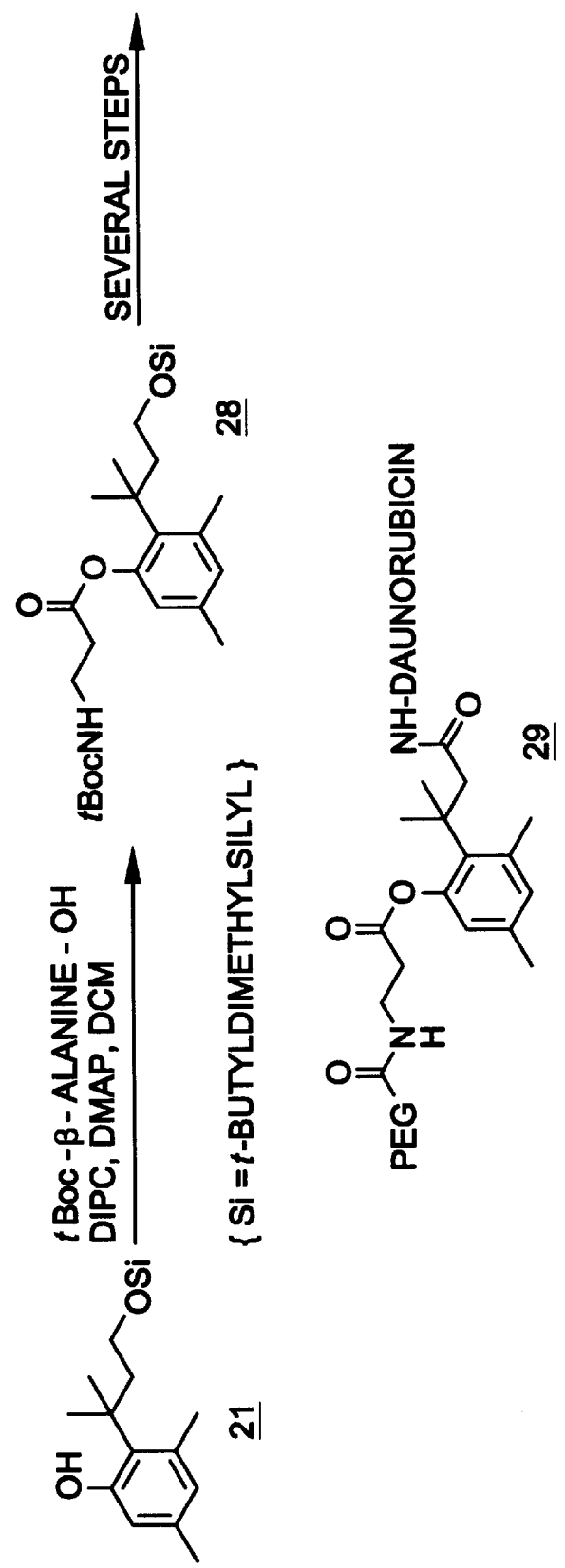
FIG. 10 illustrates the reaction scheme associated with Example 22.
Figure 11:
FIG. 11 illustrates the reaction scheme associated with Example 23.

It is certified that error appears in the above-identified patent and that said Letters Patent is hereby corrected as shown below:

Drawings:

Figure 4, sheet 4 of 11: the reactant above the arrow "THAZOLIDINE" should read --THIAOLIDINE--.

Column 6, lines 30-32: "$T_{2+e}$ hydrolysis, i.e. $T_{+e, fra\ 2+e}$ circulation>$T_{+e, fra\ ½}$ hydrolysis in plasma" should read --$T_{1/2}$ hydrolysis, i.e. $T_{1/2}$ circulation> $T_{1/2}$ hydrolysis in plasma--.

Column 10, line 33: after "Wang, et al." please insert --(-- before "Synthesis".

Claim 21, line 11: "S=" should read --S--.

Claim 28, lines 66-67: please delete the first occurrence of the term "intermediate".

Signed and Sealed this

Thirtieth Day of May, 2000

Attest:

Q. TODD DICKINSON

*Attesting Officer*          *Director of Patents and Trademarks*